United States Patent [19]

Lee

[11] 4,034,475
[45] July 12, 1977

[54] DENTAL APPARATUS

[76] Inventor: Robert L. Lee, 22937 Grand Terrace Road, Colton, Calif. 92324

[21] Appl. No.: 581,203

[22] Filed: May 27, 1975

Related U.S. Application Data

[63] Continuation-in-part of Ser. No. 485,158, July 1, 1974.

[51] Int. Cl.² .......................................... A61C 9/00
[52] U.S. Cl. ..................................... 32/21; 32/32
[58] Field of Search ..................... 32/19, 20, 21, 32

[56] References Cited
U.S. PATENT DOCUMENTS 3,206,852  9/1965  Swanson ............................... 32/22

Primary Examiner—Robert Peshock
Attorney, Agent, or Firm—Knobbe, Martens, Olson, Hubbard & Bear

[57] ABSTRACT

Jaw movements are measured mechanically and electrically. The information is used to adjust guide boxes on a dental articulator which cooperate with fixed styluses to simulate jaw movements. The information is also used to select preformed guide blocks with fixed walls. Such preformed guide blocks are adjustably mounted which causes change of the orientation of the fixed walls. Also disclosed is a hinge bracket for use in positioning preformed guide blocks for simple hinging action in an articulator. Further disclosed is a pair of alignment members having laterally extending openings which facilitate lateral adjustment of an articulator upper frame on fixed styluses of a lower frame.

24 Claims, 42 Drawing Figures

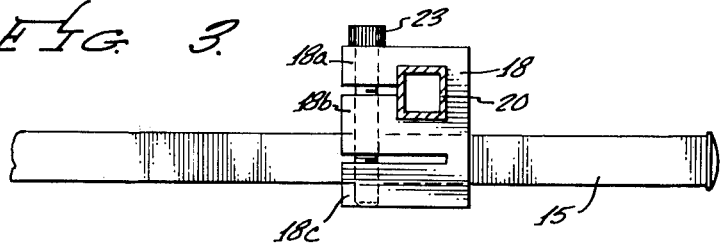
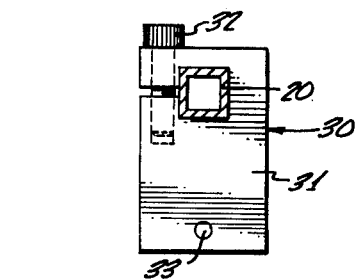
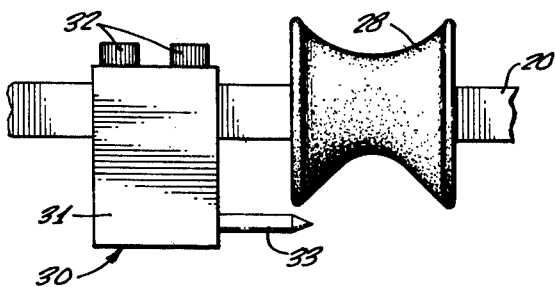
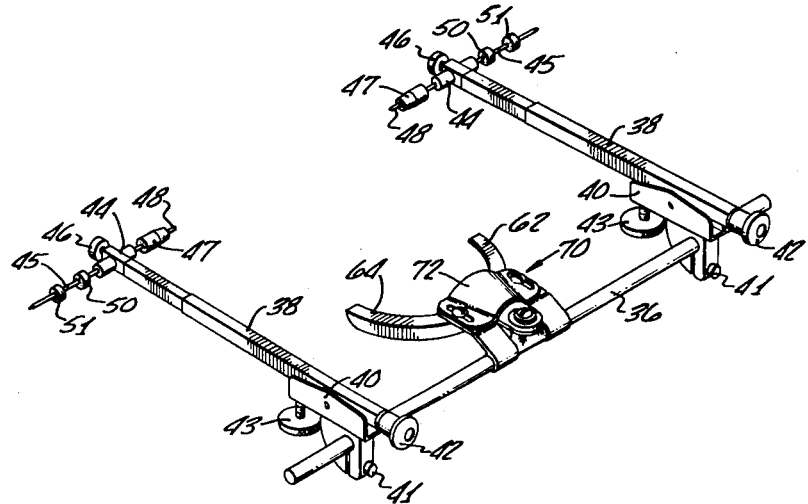

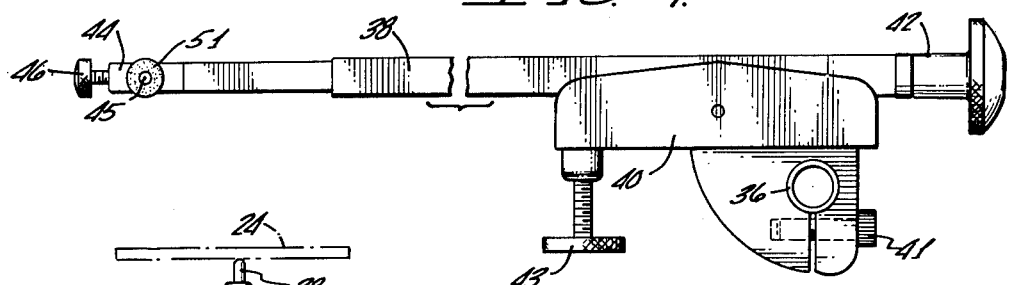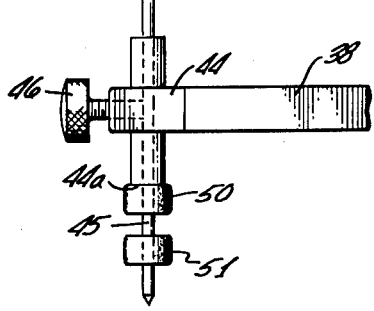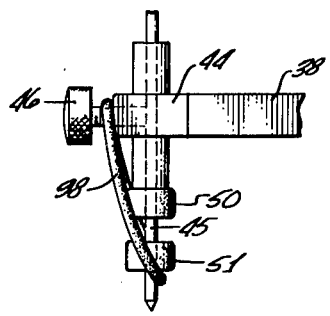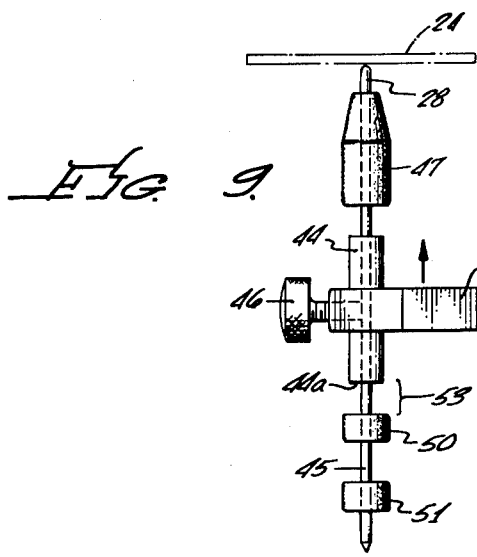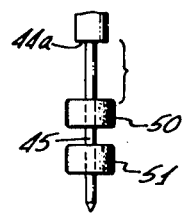

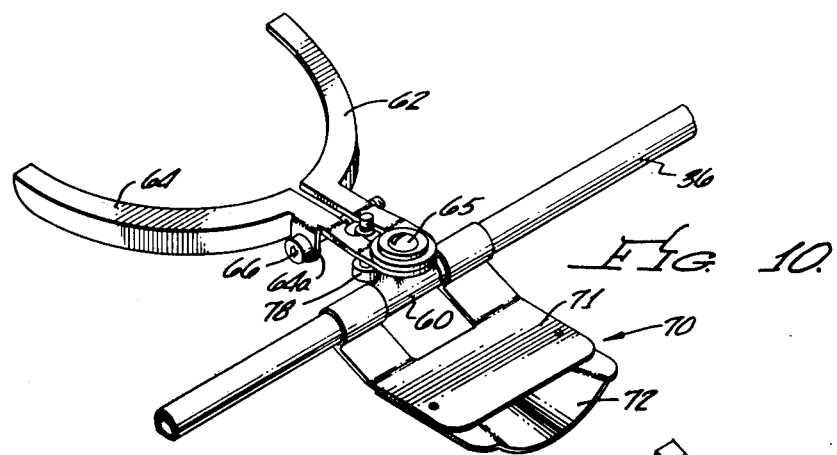
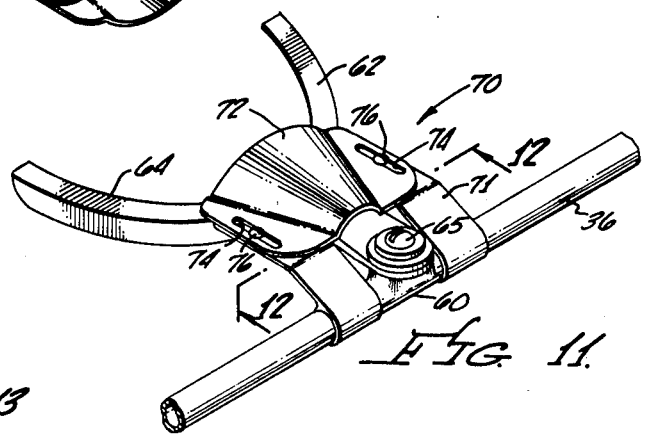
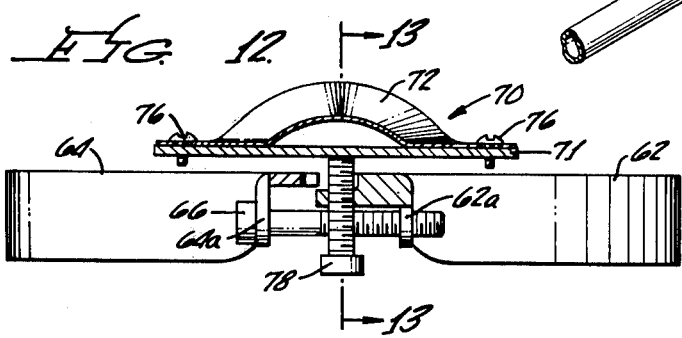
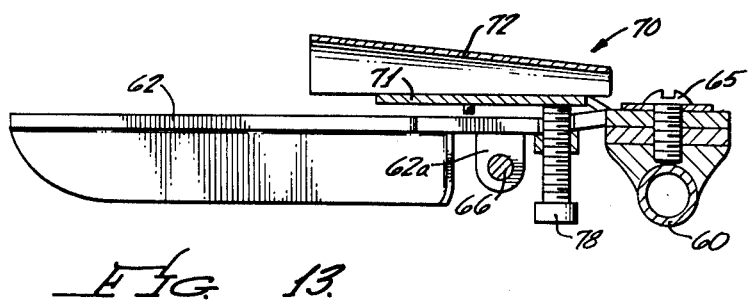

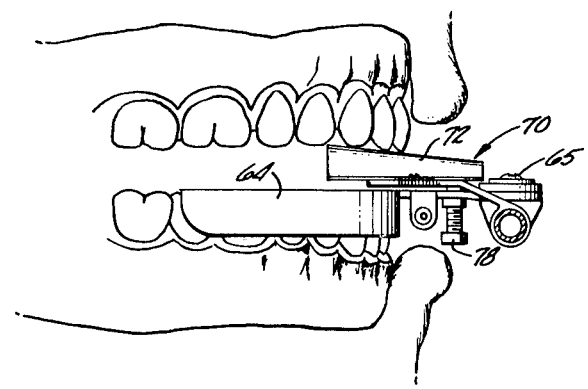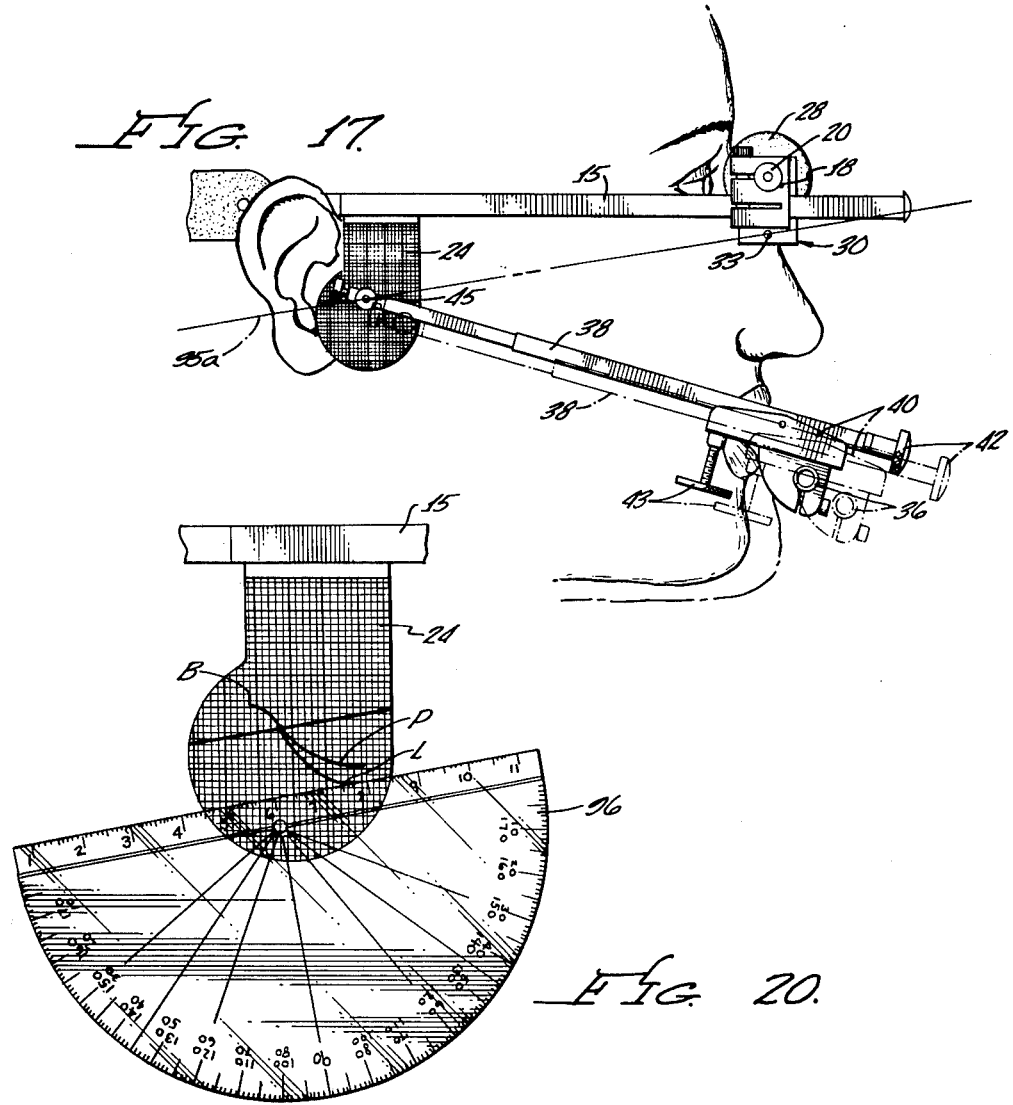

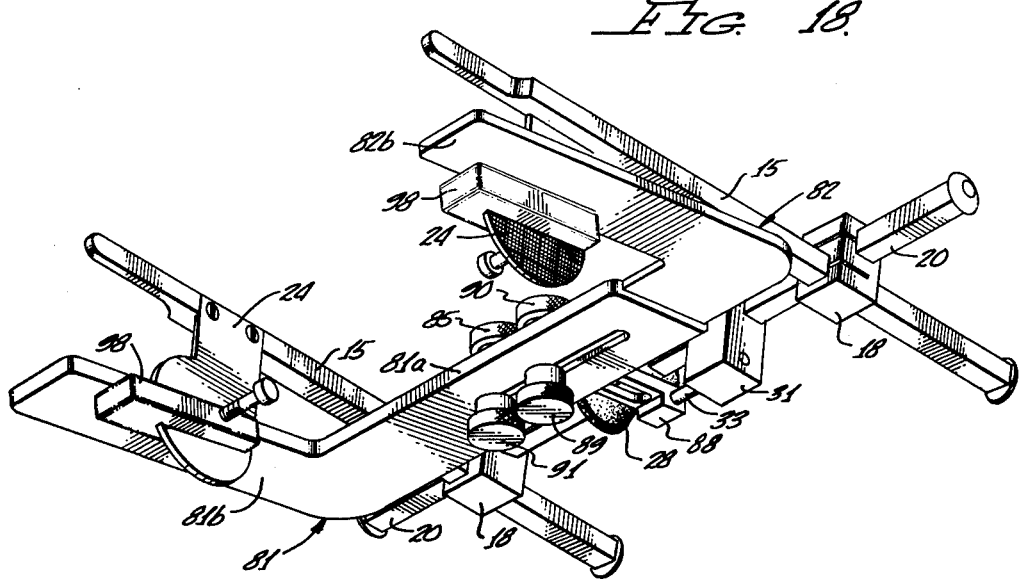
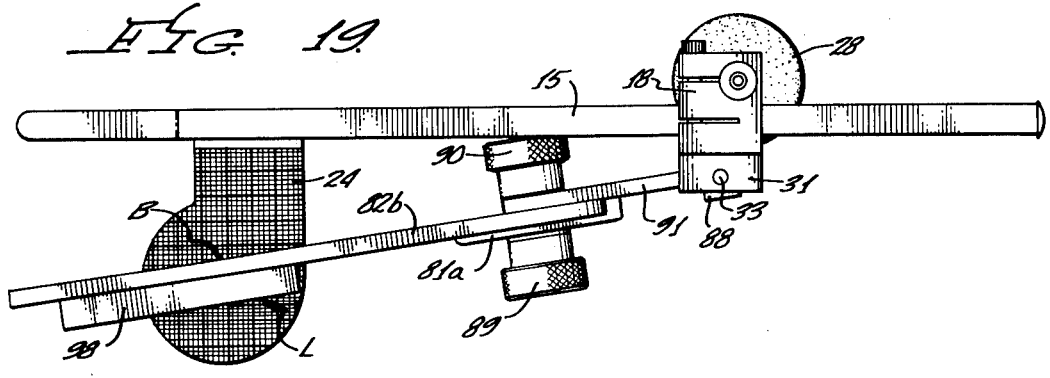

| IMMEDIATE SIDE SHIFT IN mm. | DEGREE OF SLOPE OF PROTRUSIVE PATH | DEGREE OF HORIZONTAL SLOPE OF BORDER PATH | FULL SIDE SHIFT IN mm AT 10mm FORWARD OF CENTRIC POSITION |
|---|---|---|---|
| 0mm | 30° | 45° | 5 |
|  |  |  | 7 |
|  |  | 60° | 5 |
|  |  |  | 7 |
|  | 45° | 45° | 5 |
|  |  |  | 7 |
|  |  | 60° | 5 |
|  |  |  | 7 |
|  | 60° | 45° | 5 |
|  |  |  | 7 |
|  |  | 60° | 5 |
|  |  |  | 7 |
| 1mm | 30° | 45° | 5 |
|  |  |  | 7 |
|  |  | 60° | 5 |
|  |  |  | 7 |
|  | 45° | 45° | 5 |
|  |  |  | 7 |
|  |  | 60° | 5 |
|  |  |  | 7 |
|  | 60° | 45° | 5 |
|  |  |  | 7 |
|  |  | 60° | 5 |
|  |  |  | 7 |
| 2mm | 30° | 45° | 5 |
|  |  |  | 7 |
|  |  | 60° | 5 |
|  |  |  | 7 |
|  | 45° | 45° | 5 |
|  |  |  | 7 |
|  |  | 60° | 5 |
|  |  |  | 7 |
|  | 60° | 45° | 5 |
|  |  |  | 7 |
|  |  | 60° | 5 |
|  |  |  | 7 |

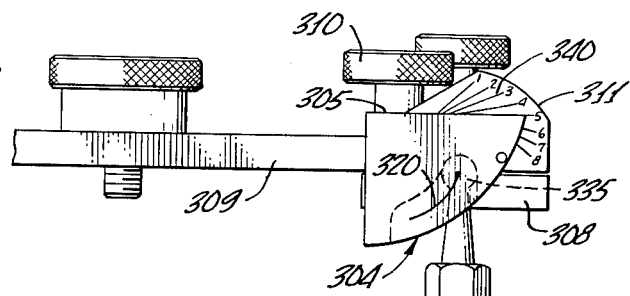
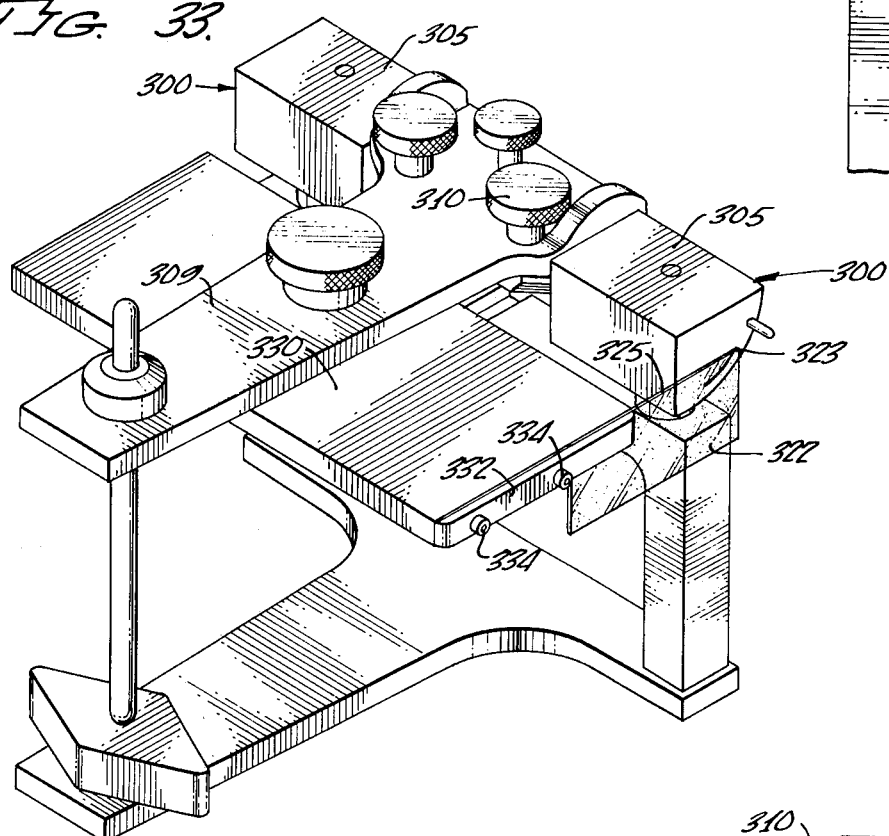
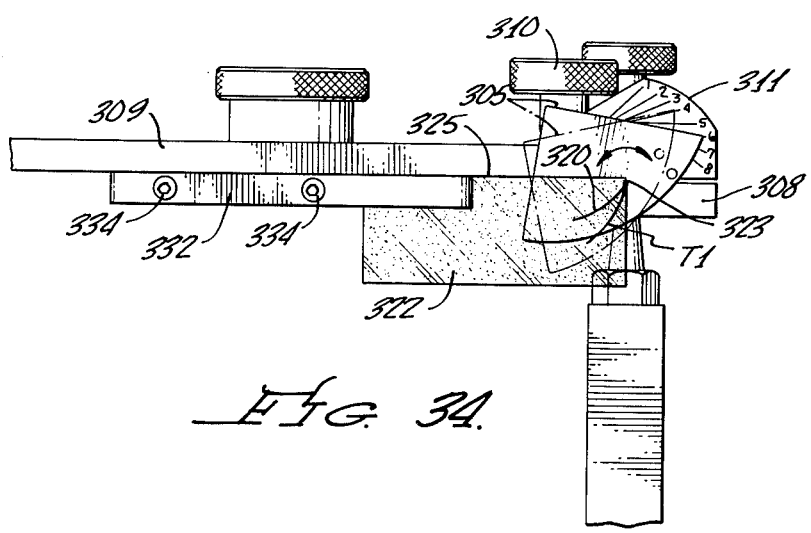

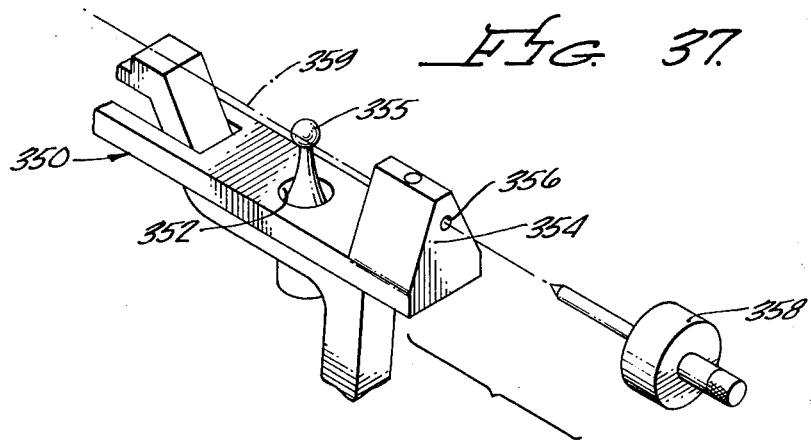
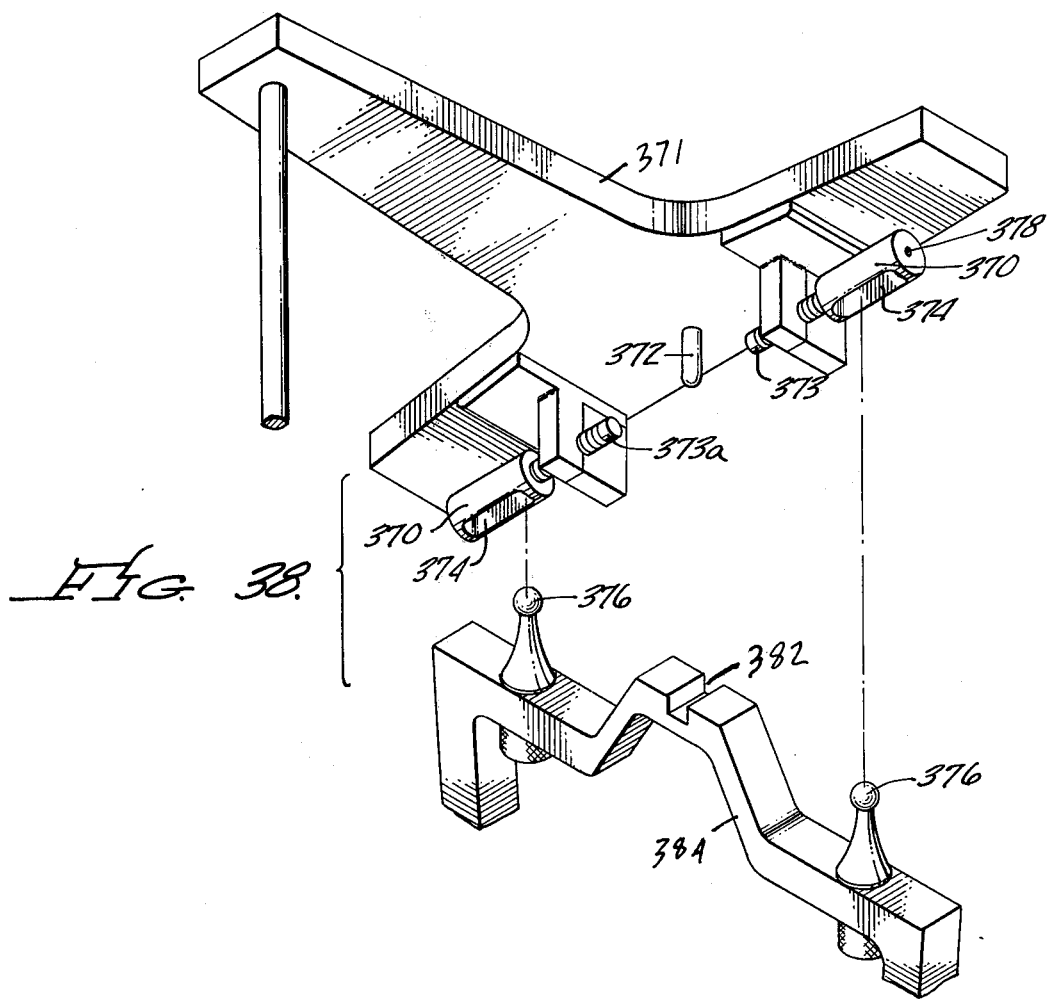

DENTAL APPARATUS

CROSS REFERENCE TO RELATED APPLICATION

This application is a continuation-in-part of application Ser. No. 485,158, filed July 1, 1974, entitled "Jaw Movement Simulation".

In the above referenced application, there is described and claimed a jaw movement simulation system including apparatus for making and recording jaw movement measurements and methods of utilizing the jaw movement measurements. This system also disclosed herein. In one method of utilizing the measurements, it is suggested that a group of standardized or average value guide blocks for use in a dental articulator be prepared. Thus, the individual dentist may make the various necessary jaw measurements utilizing the apparatus and methods described in the aforementioned Lee application and then simply select the sets of preformed analogue guide blocks which most closely approximate the patient's jaw motions. These blocks are then mounted in one frame of a dental articulator to receive styluses on the other frame to simulate the patient's jaw movements. The primary advantage of such a system is that the analogue blocks can be made by inexpensive plastic molding techniques and as a result the average dental practitioner can provide more precise or individualized treatment at a reasonable cost.

In explaining the system, it is suggested that the group of average value analogue blocks can be classified on the basis of immediate side shift from centric relation position, the degree of slope of the protrusive path with respect to a horizontal plane of reference, the degree of horizontal slope of a border path, and the full side shift at a specified distance forward of the hinge axis. While the range of precision within each group could be varied as desired, two or three classifications were suggested for each measurement with the result that in the aforementioned application 36 different types of analogue blocks might be maintained in each practioner's inventory. Although the blocks could be mass produced at relatively low cost, this approach still requires a significant inventory and space for storing it. Also the task of selecting the proper set of blocks from a range of 36 different types would have to be done with care.

The present invention relates to an alternative or improvement to the system of using preformed standardized or average value blocks. More specifically, it has been discovered or recognized that by mounting such guide blocks so that they are rotatably adjustable about the hinge axis of an articulator, the number of guide blocks required to satisfy most patients can be significantly reduced. By rotating or adjusting the guide blocks on the hinge axis, the orientation of the protrusive and sideway paths in the blocks can be adjusted as desired to best duplicate the patient's parameters. In the aforementioned Lee application, three values of protrusion path, 30°, 45°, or 60°, are suggested. By having the guide block rotatably adjusted, a wide range of path slope may be selected.

Moreover, the protrusive and sideways components of the so-called border path is also varied by rotatably adjusting the guide block about the hinge axis such that no further categories need be made for this available. It has also been found that full side shift at a specified distance forward from the hinge axis does not vary much between patients having the same or similar immediate condylar side shift, that is, the first portion of the side shift from centric relation position, which tends to have less protrusive component than the rest of the side shift. Consequently, by having the guide blocks rotatably adjustable on the hinge axis, the 36 different sets of standardized block suggested in the aforementioned application may be replaced by three sets of blocks. The resulting cost savings and simplicity of operation are readily apparent. Greater degree of accuracy may, of course, be provided by preparing different classifications of immediate side shift.

In a preferred construction, the guide block is simply provided with an axis pin molded in place in a plastic block. For ease of determining the desired angular orientation of a guide block, a path corresponding to a specified protrusive path of a stylus in the block is formed on the outer face of the guide block which is perpendicular to the centric axis. A representation of a patient's protrusive path is properly aligned over the outer face of a guide block so that the guide block may be rotated to a position where the path on the outer face of the block is aligned with that on representation. The guide block is then fixed in that position.

In one arrangement in the aforementioned Lee application, a recording of the protrusive path is drawn on a sheet of graph paper. In accordance with the present improvement, the path on the recording paper is traced onto a transparent sheet of material which is then mounted adjacent the outer face of a recording block so that the path formed on the recording block may be easily aligned with the tracing of the transparent recording sheet. The transparent sheet may be mounted to the articulator by means of a reference plate having a surface aligned with the horizontal reference plane of the articulator.

In using a dental articulator, it is sometimes desirable to be able to move the upper and lower frames relative to each other in a simple hinging action. In accordance wih another aspect of this invention, there is provided a hinging bracket which fits onto the lower frame of an articulator and includes a pair of hinge members positioned outwardly from the styluses on the lower frame of the articulator. Each of the hinge members is formed with a laterally extending opening which is aligned with the hinge axis through the two styluses. A small drill bit is inserted through the openings to form a dimple in the plastic in the preformed plastic guide blocks aligned with the hinge axis. After withdrawing the drill, an axis path may be inserted through the opening and into the dimple and then clamped in position to form a hinged support for the upper frame of the articulator.

Before mounting a pair of preformed analogue guide blocks into the upper frame of an articulator, it is often desirable to mount a dental cast on the upper frame of the articulator. For this purpose, it is necessary with certain apparatus to position a face transfer bow in alignment with the hinge axis of the upper frame. With certain articulators, the styluses on the lower frames are spaced in fixed non-adjustable distance. With such fixed styluses, the guide blocks positioned over the styluses cannot be laterally adjusted to engage the tips of the transfer face bow, since the styluses would prevent such movement. Thus, in accordance with another aspect of this invention, there is provided a pair of alignment members each having a mounting pin which is received in the upper frame of the articulator in the spaces normally occupied by the guide block mounting pins. Each alignment member has a laterally elongated slot for receiving a stylus. The slot permits the member to be laterally adjustable to the desired width to engage the transfer face bow.

Further features and advantages of the invention will be apparent by reference to the following detailed description and drawings in which:

FIG. 3 is a cross-sectional view taken along the lines 3—3 of FIG. 2 to illustrate the mounting of the transverse rod of the upper frame with respect to the side arms;

FIG. 4 is a cross-sectional view on lines 4—4 of FIG. 2 illustrating the mounting of the nose pointer;

FIG. 5 is a front elevational view of the nose pointer;

FIG. 6 is a perspective view of the lower frame apparatus;

FIG. 7 is a side elevational view of the lower frame apparatus;

FIG. 8 is a plan view of one of the styluses of the lower frame in engagement with the record plate of the upper frame with the side movement marker in its initial position;

FIG. 8a is a view like FIG. 8 with the stylus being urged against the record plate by an elastic band;

FIG. 9 is a view like FIG. 8 after the lower frame except the stylus holder has been shifted sideways on the stylus away from its marker in response to immediate side movement of the patient's mandible;

FIG. 9a is a fragmentary view of FIG. 9 showing the displacement for full side shift;

FIG. 10 is a enlarged perspective view of the tooth separator of the lower frame with the separator in the position it occupies outside of the patient's mouth;

FIG. 11 illustrates the tooth separator in its operating position;

FIG. 12 is a cross-sectional view of the separator on lines 12—12 of FIG. 11 illustrating the vertical adjustment of the separator;

FIG. 13 is a side cross-sectional view of lines 13—13 of FIG. 12 further illustrating the configuration of the separator;

FIG. 16 is a side elevational view of a patient with the tooth separator in use;

FIG. 17 is a side elevational view of the recording frames in use on the patient's head and with the protrusive movement of the mandible shown in phantom lines;

FIG. 18 is a lower perspective view of the horizontal reference plane tool positioned on the upper frame;

FIG. 19 is a side elevational view of the horizontal reference plane tool on the upper frame;

FIG. 20 is an enlarged view of a record plate with the plane of reference and the movement curves marked thereon, and a protractor for measuring the curve angle from this plane;

FIG. 32 is a side elevational view of a portion of the articulator of FIG. 30 with the opening in the guide block being shown in dotted lines;

FIG. 33 is a perspective view of the articulator of FIG. 30 showing a reference plate and a protrusion curve recording mounted thereon for properly positioning the guide blocks;

FIG. 34 is an elevational view of a portion of the articulator of FIG. 33 illustrating the manner of rotationally adjusting a guide block;

FIG. 37 is a perspective view of a portion of the bracket of FIG. 36 and a tool used with the bracket; and FIG. 38 is an exploded perspective view illustrating a pair of alignement members for use with an articulator having fixed styluses.

UPPER HEAD FRAME

Figure 1:
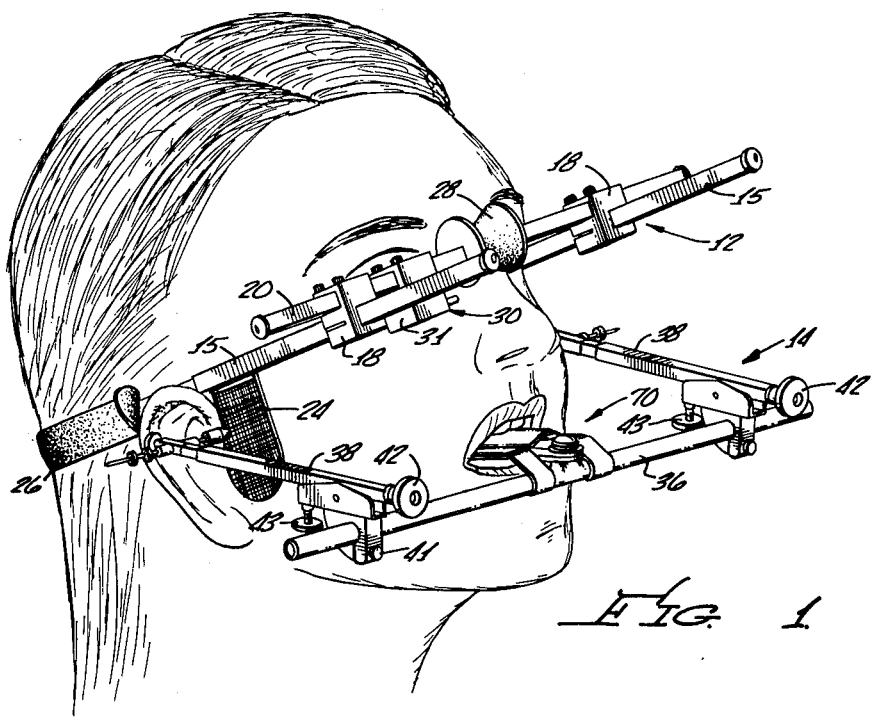
FIG. 1 is a perspective view illustrating the apparatus of the invention mounted on a patient.
Figure 2:
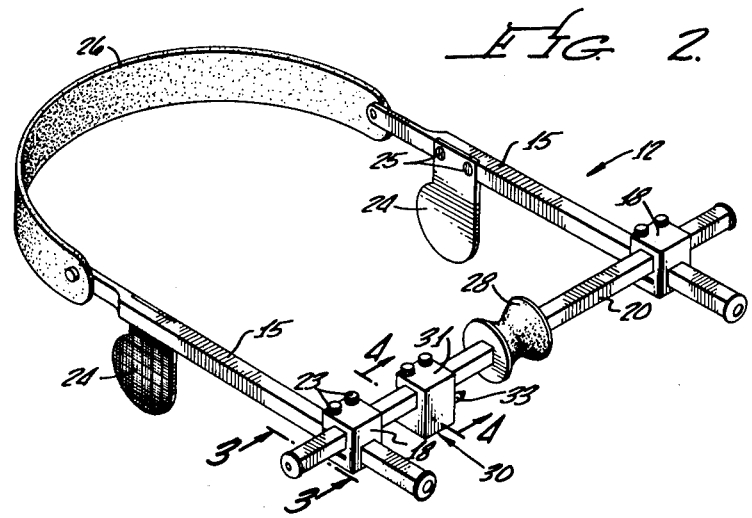
FIG. 2 is a perspective view of the upper frame apparatus.

Referring first to FIG. 1 there is shown an upper frame 12 and a lower frame 14 mounted on a patient's head 10. As can be seen the upper frame is mounted on the patient's nose and ears, while the lower frame is attached to the patient's lower jaw. Referring to FIG. 2, it may be seen that the upper frame apparatus includes a pair of side arms 15 formed of rigid materials such as metal or plastic and having a square cross-section. The side arms 15 are slidably mounted in support blocks 18. A transverse rod 20 is also slidably mounted in the support block 18 in perpendicular relation to the side arms 15. As can be seen from FIG. 3, the transverse rod 20 also has a square cross-section so that it is permanently held in perpendicular relation to the side arms even though the side arms may be moved forwardly and rearwardly to be suitably adjusted on the patient's ears and may be moved sideways to fit the width of the patient's head. Suitable clamping screws 22 and 23 extend through the block 18 to lock the side arms in a selected position. More specifically, the outer screw 22 clamps the upper and middle segment 18a and 18b (FIG. 3) of the clamp 18 to fix the side arms laterally with respect to the transverse rod 20 while the inner screw 23 clamps the upper and lower segments 18a and 18c to fix the rearward or forward movement of the side arms with respect to the transverse rod.

A stiff or rigid reference or recording plate 24 is attached to each of the side arms 15 adjacent the rear end of the arms by a pair of screws 25 or other suitable means. The plates are mounted in fixed perpendicular relation with respect to the arms 15 and 16 and extend downwardly to be positioned in front of the patient's ears as seen in FIG. 1. Each plate has a curved lower portion which extends rearwardly towards the ear so that the plate completely covers the area of the patient's temporomandibular joint when mounted on the patient's face as seen in FIG. 1. On the outer surface of each plate is grid of intersecting lines which are perpendicular to each other, and therefore the vertical lines are perpendicular to the side arms 15 and 16 and the horizontal lines are parallel to the side arms. The grid may conveniently be formed on a separate sheet of paper held by adhesive to the plate in a manner such that the sheet is readily removable from the plate. A flexible strap 26 attached to the rear end of the side arms helps maintain the upper frame of the patient's head.

Mounted on the center of the transverse rod 20 is a nasion support 28 which resets on the bridge or nasion of the patient's nose. As can be seen from FIG. 5, the support 28 has a smoothly curved central section tapering to larger diameter flanges on the ends. The curvature of the support is not symmetrical and it may be rotated on the support 20 to best conform to the patient's nasion.

Also mounted on the transverse rod 20 is a pointer assembly 30 comprising a mounting block 31 which is slidably mounted on the transverse rod 20. The mounting block 31 may be locked in a desired position by means of a screw 32 attached. A pointer 33 is mounted on the lower end of the block 31 extending generally parallel to the rod 20 towards the support 28. With this arrangement, it may be seen that the pointer is transversely adjustable on the rod 20 but remains fixed a preselected distance below the transverse rod 20 and parallel to the rod.

LOWER HEAD FRAME

Referring to FIG. 6, it may be seen that the lower head frame 14 includes a transverse rod 36 on which is mounted a pair of side arms 38. The side arms are each attached to the transverse rod 36 by a supporting unit 40 which keeps the side arms perpendicular to the transverse rod 36 while permitting them to be individually slid transversely on the rod and locked by means of a screw 41; individually moved rearwardly and forwardly by means of the adjusting screw 42; and moved angularly with respect to the transverse rod 36 by means of the adjusting screw 43 all as seen in FIGS. 6 and 7.

Positioned on the end of each of the side arms 38 is a tubular holder 44 which extends perpendicular to the side arm parallel to the transverse rod 20. A stylus, or axis pin, or other small diameter element 45 is slidably positioned in the tubular holder 44. A set screw 46 threads into the interior of the holder to lock the stylus in its desired position. On the inner end of the stylus 42 is mounted another tubular holder 46 in which is firmly positioned a scribe or writing element 48. The scribe 48 may be forcefully removed and replaced by another element or transducer. The entire system can be a writing element if desired.

On the outer end of the stylus 45 is slidably mounted a ring shaped marker 50 which is made of teflon, plastic or other suitable material which will grip the stylus 45 but yet may be manually slid on the stylus.

CLUTCH AND TOOTH SEPARATOR

Referring to FIGS. 10-13, a T-shaped support member 60 is mounted between two halves of the transverse rod 36. A pair of clutch pieces 62 and 64 are attached to the support 60 by means of a screw 65. As can be seen, each of the clutch pieces 62 and 64 includes strut portion whose forward end is attached to the support 60 and whose rearward end supports a curved portion adapted to fit over the lower teeth or gums of the patient. Each of the clutch strut portions includes a depending flange 62a and 64a. An adjusting screw 66 is threadedly mounted in the flanges so that the spacing between the clutch piece 62 and 64 is laterally adjustable by means of the screw 66.

Pivotally mounted on the transverse rod 36 is a tooth separator base plate 70. More specifically, the base plate 70 includes a pair of arms straddling the clutch support member 60 and which fit over the transverse rod 36 so that the base plate is swingable about the rod. The base plate 70 further includes a flat portion on which is mounted a separator or contact element 72. The separator element has a pair of side flanges with elongated mounting slots 74 which receive screws 76 threaded into the separator base plate 70. This arrangement of course permits front to rear adjustment of the separator elements 72 with respect to the base plate 70. The upper surface of the separator element 72 is smoothly curved into an arch shape from side to side as seen in FIGS. 11 and 12. Also, as seen by FIG. 12, the element 72 slopes downwardly in the forward direction. The patient's upper teeth or gums engage the upper surface of the separator element 72. The height and shape of the arch may be selected to best fit the patient's mouth. Various separator elements may be employed since they are readily separable from the base plate 70.

As may be seen from FIG. 10, the separator may be swung out of operating position, or may be positioned in operating position as shown in FIG. 11. In this latter position, the base plate 70 is supported by an adjustable screw 78 which is threadedly mounted in the strut portion of the clutch element 64.

STRAIGHT EDGE TOOL

Figure 14:
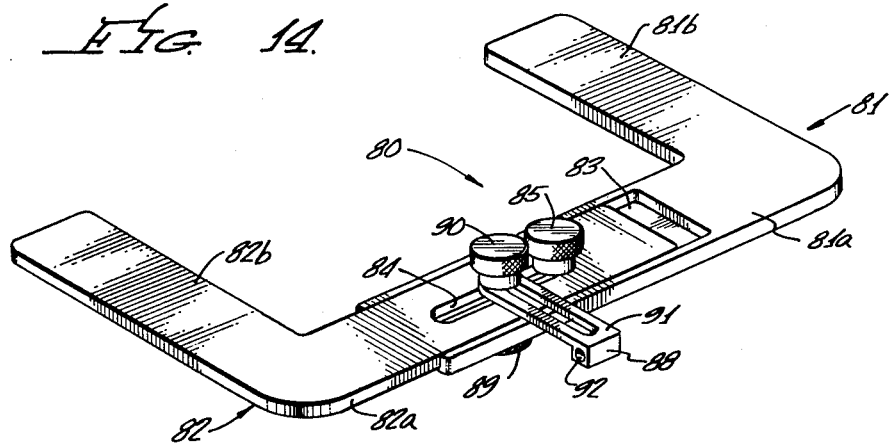
FIg. 14 is a top perspective view of a tool for locating the exact horizontal plane of reference formed by the jaw hinge axis and a point of the patient's nose.

Referring now to FIG. 14, there is shown a straight edge tool 80 to be used with the upper frame for marking the horizontal plane of reference for the jaw movements measured. As can be seen, the tool has a generally U-shape formed by two L-shaped flat plates 81 and 82. The right plate 81 as seen in FIG. 14 has a recess in its transverse leg 81a which receives the transverse leg 82a of the left plate. The depth of the recess is equal to the thickness of the left plate so that the upper surfaces of the two plates are in the same plane. The recess 53 in the right plate permits lateral adjustment of the plates so as to vary the distance between the rearwardly extending parallel legs 81b and 82b of the plate. To lock the plates at the selected position, there is provided an elongated slot 84 in each of the overlapping legs 81a and 82a of the plates with said slots being aligned so that a bolt 85 extends through the slots and a locking nut 86 is threaded onto the bolt to clamp the plates to each other.

Figure 15:
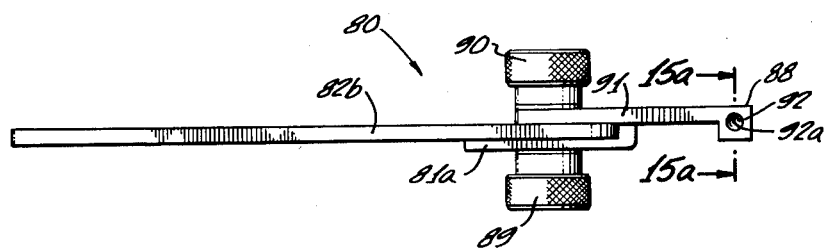
FIG. 15 is a side elevational view of the tool of FIG. 14.

A pointer receiving element 88 is clamped to the tool by means of another nut 89 and bolt 80 combination extending through the slots 84 in the left and right plates. Thus, the element is laterally adjustable by moving the bolt 90 laterally. The element also has an elongated slot 91 formed therein which permits it to be adjustable from front to rear, or angularly. Formed in one edge of a depending lug at the forward end of the element 88 is a dimple 92 for receiving the pointer 33 on the upper frame. As can be seen from FIG. 15, the center 92a of the dimple is precisely aligned with the upper surface of the plate of U-shaped tool 80 so that the dimple is in the same plane with the upper surface.

OPERATION

As the first step for utilizing the apparatus of the invention, the lower frame 14 without the side arms 38 is attached to the patient's mandible. The clutch elements 62 and 64 shown in FIG. 10 are laterally adjusted by means of the adjusting screw 66 to fit the patient's lower jaw. The tooth separator 70 should be swung to the position shown in FIG. 10 where it is not in operating position. The lower side of the clutch elements 64 and 62 which extend into the patient's mouth is then filled with a denture compound or plastic. While the compound is still pliable the clutch is inserted into the mouth over the lower teeth so that the compound is pressed onto the buccal surfaces of the teeth. After the compound hardens the clutch may be removed from the teeth. Denture paste is then inserted into the compound and the clutch is reinserted over the lower teeth. After several minutes, the paste will have hardened so that the clutch attached to the transverse rod 36 is securely fixed to the teeth.

The upper frame 12 is now positioned on the patient. The set screws 21 and 22 are loosened so that the apparatus may be positioned over the patient's head. The nasion positioner 28 is rotated to fit the particular shape of the nose. The patient holds the nasion positioner against the nose while the operator moves the side arms 15 and 16 inwardly towards the patient's head and front to back, until the grid plates 24 are positioned just in front of the ears and the side arms fit snuggly against the side of head. The rear portion of the side arms rest next to the head on top of the ear. The set screws 21 and 22 are now tightened in this position to hold the side arms in fixed relation perpendicular to the transverse rod 20. The elastic strap 26 attached to the ends of the side arms is positioned around the back of the head to help hold the upper frame in proper position.

The pointer 33 which is previously loosened on its mount is moved transversely to engage the patient's nose a predetermined distance below the transverse rod 20, and the pointer is then locked in such position.

The adjustable side arms 38 of the lower frame 14 are now slid onto the lower transverse rod 36 and moved inwardly until the writing elements 48 engage the grid on the recording plates 24. Note that the lateral or outer ends of the scrib holders 47 must be spaced sufficiently from the stylus supports 44 to allow for lateral jaw movements. Four to five millimeters should accommodate any such movement.

As a next step, the patient's hinge axis in centric relation position should be located. The tooth separator 70 is swung inwardly into the patient's mouth so that the patient's upper front teeth or ridge will engage the upper surface of the curved separator element 72 as may be seen in FIG. 14. The patient's mandible is opened and closed while in the terminal hinge position, that is, where the lower jaw is in its most rearward position. It is important that the back teeth be slightly separated in that the muscles of the jaws tend to draw the lower jaw into its rearwardmost position, but the rear teeth could act as a fulcrum and interfere with this action if the upper and lower teeth are not separated. Thus it would be more difficult to keep the lower jaw in its hinge axis position.

As the patient's mandible is moved up and down in the terminal hinge position, the side arms 38 of the lower face bow 14 should be adjusted vertically and from front to back until the writing elements, or scribes 48 no longer arc, but simply rotate. The grid lines on the plates 24 are helpful in this step as they act as references. This is the point where the hinge axis exits from the head and is the starting point for the recording measurements. Consequently, with the side arms 38 so positioned, the set screws for positioning the side arms are locked so that the scribes 48 are fixed in aligned relation with the patient's hinge axis. This point is illustrated at 93 in FIG. 20.

To measure the protrusive movement, the patient's mandible is placed in the terminal hinge position or centric relation position and the two axis styluses 45 are pushed inwardly so that the scribes 48 are tightly against the grid plates 24. The styluses are then locked with the set screws 46. The patient then protrudes the lower jaw while the two scribes 48 trace a path P of the protrusive movement of the grids. Since the upper wall of the human temporomandibular joint usually slopes downwardly, the patient's condyles will usually move downwardly as they move forward. This is indicated in phantom lines in FIG. 15. Because of movement in this fashion, the path P traced on the grids slopes or curves downwardly as shown in FIG. 20. The slope of this downward and forward curve may be read on a suitable reference line on the grid.

While the angle of protrusive movement may be measured with respect to a horizontal line on the grid which is parallel to the side arms of the upper frame, it is preferable that the angle be measured with respect to the true horizontal plane of reference formed by the terminal hinge axis position and the point which is located on the side of the patient's nose by the pointer 33. This is preferred because this is the reference plane used for mounting denture casts in an articulator.

Figure 15A:
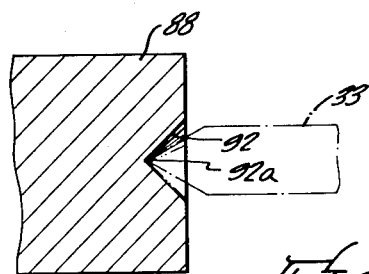
FIG. 15a is a cross-elevational view of the dimple of FIG. 15.

The reference plane straight edge or tool tool 80 is used to physically mark the plane on the grid paper on the plates 24, as shown in FIGS. 18 and 19. More specifically, after the protrusive and lateral jaw movement curves P and L, FIG. 20, are marked on the grids, the upper frame 12 is removed from the patient and the U-shaped reference plane tool 80 is positioned to straddle the arms 15 and the recording plates 24 on the upper frame. The legs of the U-shaped tool are laterally adjusted so that they just engage the outer sides of the recording plates 24. The pointer 33 is positioned in the dimple 92 formed in the element 88 attached to the reference plane tool as shown in FIG. 15a. Note that the element 88 can be adjusted laterally and rearwardly to easily receive the pointer. With the forward end of the tool so positioned by the pointer, one leg of the tool is aligned on the recording plate 24 which it engages so that the hinge axis point 93 is in the reference plane forming the upper suface of the tool. The tool is temporarily clamped in this position by the suitable clamp 98 shown in FIG. 16. The other leg of the tool is then similarly positioned on the outer recording plates. By using the tool as a straight edge, a line 95 can then easily be drawn on the grip paper on the recording plate through the hinge axis 93 to represent the reference plane, shown as 95a in FIG. 17. Such a reference line 95 can be marked on both the grids. The reference plane tool 80 is then removed so that the protrusive angle can be readily measured with a protractor 96 or other similar tool.

It will be noted that the slope of the protrusion curve P changes. Thus, it can be measured at any number of points as desired or can be constantly monitored. If comparisons are desired between recording plates of various patients, a standard measurement point with respect to the hinge axis point 93 can be selected.

Referrring to FIGS. 8 and 9, another measurement to make is the side shift or lateral displacement of the condyles when the jaws is moved to one side as in chewing. First, the mandible is placed in centric relation position. Second, the stylus is pushed inwardly until the writing tip touches the recording plate. Third, the adjustable screw 46 is tightened to lock the stylus 45 and the marker 50 is slid inwardly on the stylus 45 until it is engaging the outer or lateral surface 44a of the holder 44, as seen in FIG. 8. Next, the adjustable screw 46 locking the stylus 45 with respect to the holder 44 is loosened on one side of the lower frame. The mandible is then moved directly laterally to the extent possible in the direction to move the side of the lower frame on which the screw 46 has been loosened toward the adjacent recording plate. In other words, referring to FIG. 9, the arm 38 is moved, as indicated by the arrow, toward the recording plate 24. The stylus 45 cannot move in that direction because its inner end 48 is in engagement with the plate 24 on the fixed upper frame. Instead, the holder 44 on the arm 38 slides inwardly on the stylus 45. The marker 50 remains fixed on the stylus 45 and thus the reference surface 44a is spaced from the marker 50. It is a simple matter to measure the displacement 53 of the holder 44 which represents the direct or immediate mandibular side shift in one direction. A similar procedure is followed to obtain the side shift in the other direction.

Also the so-called full mandibular side shift is obtained in this manner but the mandible is allowed to make a more complete side chewing movement. During a full chewing movment, the mandible moves fowardly as well as laterally. The border of this combined movement can be recorded by having the stylus 45 trace the path of the hinge axis motion on the vertical plates simultaneously with the side shift measurement. For this purpose, an elastic or small spring 98 shown schematically in FIG. 8a is employed to urge the stylus against the plate at all times so that a tracing is obtained. The elastic 98 extends between the holder 44 and the outer element 51 tightly mounted on the stylus 45. Referring to FIG. 20, the path L of this full chewing movement usually has a steeper slope than that of the protrusive movement P.

As the hinge axis moves during a side chewing movement producing downward and forward slope on one side of the head as evidenced by the path L, the stylus on the other side of the head representing movement of the other end of the hinge axis is moved upwardly and rearwardly a small amount. This path which is shown on FIG. 20 as B and often referred to as backlash, is caused because the tip of the scribe recording the path is spaced laterally from the condyles within the head.

While the border path of the side chewing movement is being recorded on the grid record plate 24, the cmplete side displacement is being measured by the markers 50 being displaced relative to the reference surfaces 44a on the holders 44. By returning the mandible back to centric position, the displacement is easily measured. This displacement is shown at 55 in FIG. 9a as typically being considerably greater than the immediate side shift 53 in FIG. 9.

ELECTRONIC MEASURING MEANS

Figure 21:
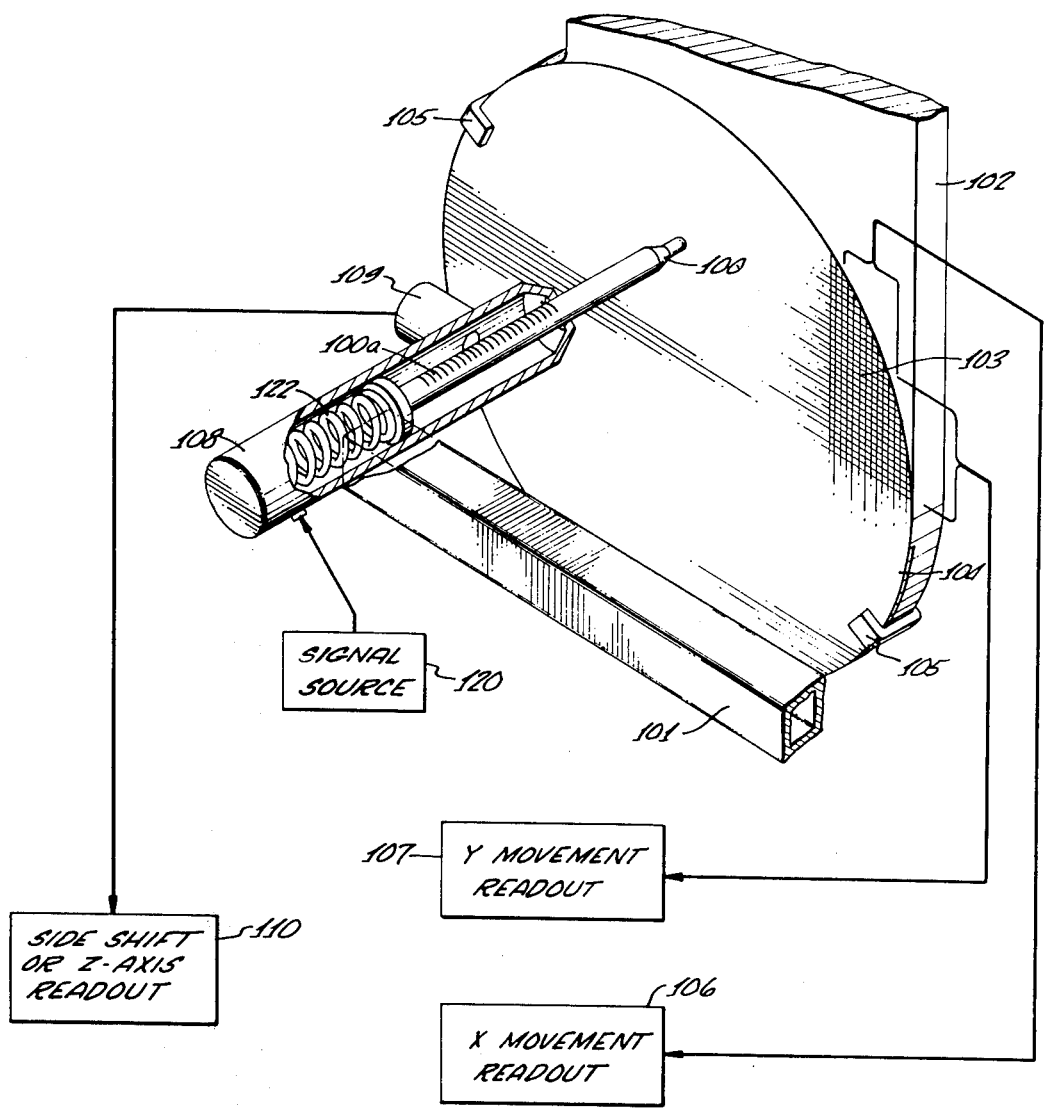
FIG. 21 is a schematic perspective view of apparatus for electronically monitoring jaw movements.

As mentioned above the movement of the styluses 48 may be monitored electronically as well as mechanically. Such an arrangement is schematically illustrated in FIG. 21 wherein the stylus is in the form of a current inducing probe 100 supported on an arm 101 of a lower frame, and connected to a signal source 120. A recording plate 102 attached to the upper frame has a grid 103 of insulated electrical wires embedded in a thin sheet 104 rotatably supported on the surface of the recordng plate by three clips 105, which grip the sheet 104 but permit limited rotation in order to align the grid with the true horizontal reference plane. The sheet 104 is transparent on its outer surface so that the wires are visible and can serve as alignment grid lines. Also the sheet is sufficiently self-supporting so it remains flat when supported on its edges in the vertical orientation shown.

As the patient's jaw is moved into protrusive position, the probe 100 is moved adjacent the surface of the sheet 104 inducing current in the grid of wires 103, as the probe crosses a wire. These current signals are sensed and recorded, on suitable readouts, indicating the movement on the surface of the recording plate. In the arrangement shown, the signals produced in crossing the vertical wires, that is, moving horizontally, or in the X axis direction, are displayed on an X-movement readout 106 and the signals resulting from a crossing of the horizontal wires, that is, moving vertically, or in the Y axis direction, are displayed on a Y-movement readout 107. The output may be shown on counters or they may be combined and shown on an oscilloscope type display, if desired. In either event the position of the probe along the surface of the record plate is thereby monitored.

The details of the current inducing probe, the grid, and the readouts are not disclosed herein in that such position identifying devices are prior art. For example, U.S. Pat. Nos. 3,461,454 and 3,647,963 each disclose systems that could be adapted to this purpose. Moreover, there are a variety of digitizers known in the prior art which could be utilized in such an application.

In use, the arm 101 of the lower frame is adjusted until the hinge axis is located, and the arm is then fixed to the transverse rod 36 of the lower face bow. The hinge axis is located when arcuate movement of the probe 100 stops, as indicated by the X and Y readouts 106 and 107, as the mandible is opened and closed. Before protrusive movement is commenced, suitable adjustments may be provided to make the protrusive movement readings measurable with respect to the reference plane 95a defined by the hinge axis and the pointer 33. As one approach, a reference plane tool (not shown) similar to the tool 80 but adapted to be positioned over the upper face bow while the bow is on the patient is then aligned with the probe 100 and the nose pointer 33, FIG. 18. The grid sheet 104 is then rotated so that its horizontal lines are parallel with the planing tool. The plane tool is then removed, the readout set to zero; and protrusive movements commenced. The slope of the protrusive curve can be determined from the readout information on the XY axes of the grid. It should be noted that this method of having the grid sheet rotatable to align the horizontal lines on the grid with the reference plane 95a can also be used in the mechanical arrangement discussed above.

For measuring the side displacement of the lower jaw, or in other words, the movement of the lower frame in the lateral or outward direction, other known plotting arrangements may be employed. For example, the probe 100 is urged against the grid 103 by a spring 122 confined in a holder 108 which supports the probe 100 and is attached to the side arm 101. A transducer unit 109 mounted on the holder 108 adjacent the probe 100 is provided to measure the lateral movement of the holder with respect to the probe. The probe is provided with suitable markings 100a which are monitored or counted by the transducer unit 109. The output of the transducer is transmitted to a suitable Z axis readout 110 for indicating side shift. The transducer 109 is well known in the art, one such arrangement comprising a light source, a small metrological grating, and a photosensitive cell. The output of the photosensitive cell is a series of pulses; each pulse indicates that the holder has moved a predetermined incremental distance. Further details regarding such a sensing arrangement may be found in U.S. Pat. No. 3,434,218. It should be understood that a variety of methods are known for monitoring and measuring such movement electronically. This horizontal or lateral motion, monitored on the so-called Z axis, can be syncronized with the signal from the XY positions so as to give a changing positional reading of the probe tip in relation to the XYZ axis of its starting position. In other words, at any given point in time in a specific jaw movement, the stylus tip position can be determined with respect to the horizontal reference plane by the X, Y, Z coordinates.

USE OF JAW MOVEMENT INFORMATION a. Jaw Movement Simulators

With the apparatus and methods described above, jaw movements are readily measured. Such information is useful for properly adjusting dental articulators which are utilized to simulate jaw movements. That is, the side shift, immediate and full, and the slope of the upper wall of the guide boxes used for controlling articulator movement can be set. For example, referring to FIGS. 22 and 23, there is shown a dental articulator or jaw movement simulator including a lower frame or assembly A and an upper frame or assembly B which respectively represent the lower and upper jaws of a human for simulating jaw movement. In the position illustrated, the upper assembly B can be pivoted on the lower assembly A which is reverse to the human mandible or lower jaw which slides with respect to the maxilla or upper jaw, however the relative motion between the two frames is the same.

The lower assembly A includes a generally T-shaped base member 210 having a forward arm 211 and an incisal pin rest pad 212 mounted thereon. Mounted on top of the rear of the base member 210 is a vertical frame member 220 supporting a pair of spaced spherical styluses 225 which represent the simulated horizontal or hinge axis of the condyles of a human. A screw 231 projects upward through an opening in the arm 211 for attaching a dental mounting plate schematically illustrated at 232.

The upper assembly B of the articulator includes a T-shaped upper frame member 240 having lateral slotways 245 in its transverse arm 242. Attached to the forward end of the forward arm 241 is an incisal rest pin 260 which has its lower end supported on the upper surface of the rest pad 212 on the lower assembly. A horizontal flag 264 used to indicate the horizontal plane of reference is attached to the forward end of the arm 241 immediately to the rear of the incisal pin 260. The undersurface of this flag forms a horizontal plane with the hinge axis through the styluses 225 when the guide housings are at centric relation position. The forward arm 241 is adapted to receive a mounting plate for a maxillary dental cast schematically illustrated at 252 in FIG. 22.

Figure 23:
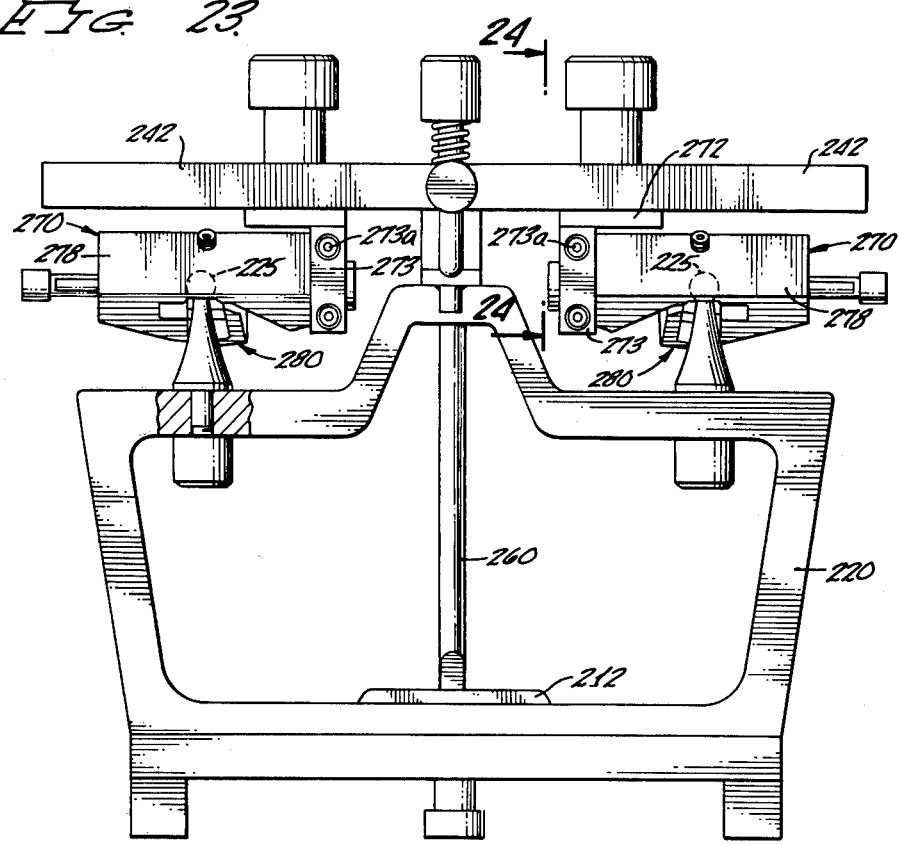
FIG. 23 is a rear elevational view of the instrument of FIG. 22.
Figure 24:
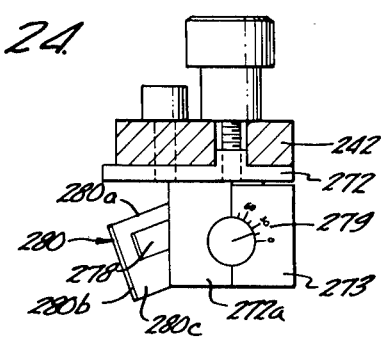
FIG. 24 is a cross-sectional view on the line 24—24 of FIG. 23 illustrating the adjustable mounting for one of the guide boxes.
Figure 25:
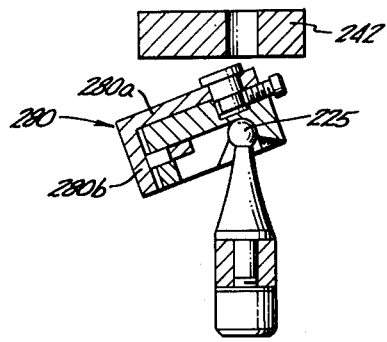
FIG. 25 is a cross-sectional view on the line 25—25 of FIG. 23 illustrating the adjustable mounting of the medial wall of the guide box.
Figure 26:
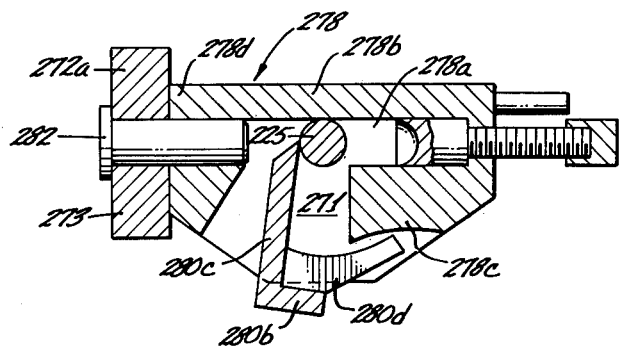
FIG. 26 is a cross-sectional view on line 26—26 of FIG. 25 illustrating the shape of the guide box.

Attached to the outer arms 242 of the upper frame assembly are a pair of guide assemblies 270 which cooperate with the styluses 225 of the lower frame. Attached beneath the arm 242 for each guide assembly is a mounting plate 272 having a trunion portion 272a (FIG. 24) to which is attached a mating trunion member 273 by suitable fastening elements 273a seen in FIG. 23. Each guide assembly 270 includes a pair of irregular five wall guide boxes 271 whose walls are formed by a primary guide housing 278 and a secondary member or housing 280. Referring to FIG. 26 as well as to FIGS. 22-25, the primary guide housing 278 has a generally flat upper wall 278a, a generally flat rear wall 278b, and a generally flat outer wall 278c. The primary guide housing 278 also includes a mounting end 278d having a retained cup-end shaft or pin 282 which is gripped by the trunions 272a and 273. The primary guide housing 278 is joined to the pin 282 to act as one piece, and hence the entire guide housing can be rotated horizontally as desired with the pin 282 and clamped in this position by means of the fastener 273a. An angular scale 279 is formed on the trunion 273 as shown in FIG. 24 to indicate the angular orientation of th guide housing 278 to the horizontal plane. Thus the general slope of the protrusive path 94 shown in FIG. 20 is used to set the angle of the guide housing 278, the information being measured by the protractor 96 or shown on the electronic readout 106 and 107 of FIG. 21.

Figure 27:
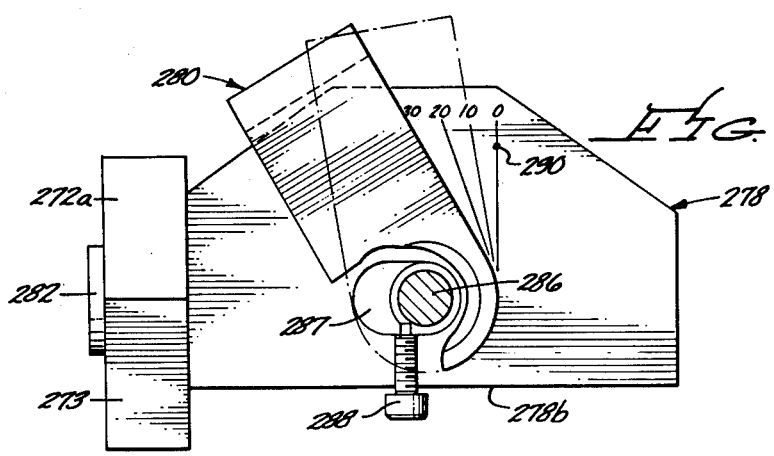
FIG. 27 is a top view of a guide box showing the adjustablity of the medial wall.

The secondary guide housing 280 is an irregularly shaped element preferably formed as an integral piece which fits onto the primary housing 278. The secondary housing 280 includes a horizontally flat upper support arm 280a, (when viewed in the orientation of FIGS. 22 and 25) a vertical wall 280b, a flat vertically oriented but horizontally extending wall 280c attached to the vertical wall 280b, and a generally flat, curved, finger-like front guide wall 280d extending outwardly from the walls 280b and 280c. The flat support arm 280a is mounted on the primary guide housing with a pivot pin 286 by means of a set screw or other suitable means not shown. Referring to FIG. 27, the opening 287 through which the pin 286 extends is elongated laterally so that the pin 286 carrying the inner guide wall 280c may be moved inwardly a small amount, such as about two millimeters. An adjustment of this type for both right and left guides thus may provide a total horizontal side shift of 4 millimeters. A set screw 288 extending through the rear wall 278b of the primary guide housing 278 engages either one side or the other of the pivot pin 286 to laterally fix the pin 286 and the secondary guide housing 280 and also to prevent rotation once the desired angular setting of the inner wall 280c has been made. The vertical support wall 280b of the secondary housing 280 extends adjacent the forward edge of the housing 278 and the internal surface of the horizontally extending vertically oriented wall 280c forms the inner or medial surface for the guide box 71.

Thus, the side shift information obtained as discussed above in connection with FIGS. 7–9 is used to set the lateral position of the pin 286 in the slot 287. Structure to provide fine degrees of adjustment may be utilized if desired. The angle of the member 280, and thus the angle of the medial wall 280c of the guide box is set by using side shift measurement (Z axis) and forward movement information (X axis) during a chewing operation. Referring to FIG. 27, the X axis information is measured in the forward direction on the 0 angle line, and the Z axis information is measured perpendicular to the 0 angle line. In the case of the elecronic measuring means, the X and Z readings are conveniently available at any point, and can be scaled off on the guide housing at any point in setting the member 280. In the case of th mechanical arrangement, the maximum or full side shift, as determined above in reference to FIGS. 7–9, has been found to be near where the paths P and L of FIG. 20 stop moving downwardly or in the Y direction. The full chewing side shift is typically obtained at about the ten millimeter mark on the X axis. Thus a mark 290 may be conveniently formed on the zero angle line on the upper side of the guide housng 278 ten millimeters from the hinge axis in centric position through the center of the pin 286, as shown in FIG. 27, and the full side shift measurement utilized at that point to position the member 280. A scale for full side shift may be marked on the member 280 if desired.

In some articulators available, the slope of the upper surface 278a of the guide box adjacent the medial wall 280c can be separately adjusted. Information for this is obtained from the slope of the curve L in FIG. 20 or from the electronic readout on the XY axes while in side chewing position. Also some articulators can make adjustments for backlash B and this information is available from the grid plate in FIG. 20 or from the electronic readout.

b. Preformed Analogue Guide Blocks

Figures 28, 29:
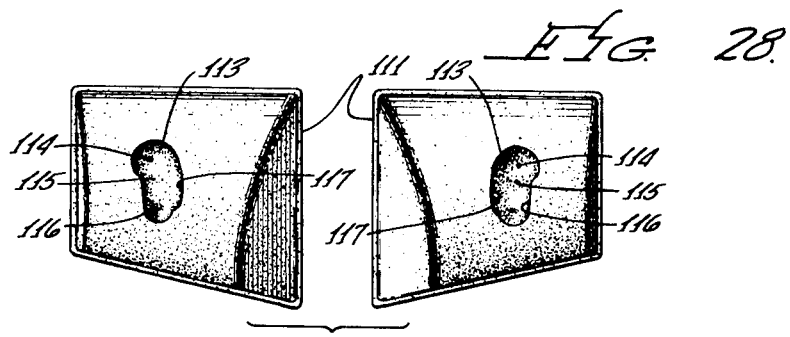
FIG. 28 is a perspective view of a set of analogue blocks having openings for guiding an articulator lower frame to simulate a mandibular movement.
FIG. 29 is a chart illustrating use of performed standarized analogue blocks.

The information obtained may also be utilized for preparing or selecting openings in analogue guide blocks which when used with an articulator in place of the guide boxes 271 of the simulator in FIGS. 22–27, more precisely duplicate or simulate the joint movements. One such set of blocks 111 having openings 113 is shown in FIG. 28, by way of example.

For convenience of comparison, the guide blocks 111 are shown oriented similar to the guide boxes 271 of the simulator shown in FIG. 26. While the guide boxes are straight line and have generally planar walls, the walls of the guide blocks are usually curvilinear and thus more accurately provide movement simulating the patient's jaw movement. The points 114 in FIG. 28 mark the location of the styluses 225 of FIG. 26 when positioned in the five-sided irregularly shaped guide block pathways or openings 113 in centric relation. The upper wall 115 of the guide blocks corresponds to the wall 278a of the guide boxes 271, while the lateral wall 116 and medial wall 117 correspond to the guide box walls 278c and 280c respectively.

U.S. Pat. No. 3,452,439 issued to Robert L. Lee discloses a procedure of machining a special set of analogue blocks for each patient. Such blocks are highly accurate in that the individual patient's jaw movement information is used to form the opening or pathway 113 which will closely simulate or duplicate the patient's jaw movements. The shortcoming of this procedure is that it is somewhat expensive. Such blocks have now been made on a relatively large number or patients and the characteristics of these blocks have been analyzed. This analysis discloses that most of the joint movements may be classified into a relatively small number of categories. For example, by classifying the pathways of the analogue blocks into just three variations of immediate side shift and three variations of the slope of the protrusive curve, nine relatively broad categories are created. FIG. 29 is a table introducing two other variables for a total of thirty-six categories. The first column indicates immediate side shift of zero, one millimeter and two millimeters. The second column indicates the slope of the protrusive curve at a selected location in 15° increments of 30°, 45° and 60°. Column 3 lists the horizontal slope of the lateral or border path as 45° or 60°. Column 4 specifies the full side shift in one, two, three or four millimeters at ten millimeters foward from centric, which determines the angle of the medial wall. In other words, the full side is the intermediate side shift plus 1 or 2 millimeters.

By selecting these broad categories, analogue blocks having such characteristics can be prepared in large quantities. A main advantage of this arrangement being that if only certain standarized sizes are utilized, the blocks can be made by inexpensive manufacturing techniques such as molding. Thus, when the jaw movement parameters of a patient are measured it is a simple matter to select a set of blocks which most closely fit these measured parameters. The cost of the blocks are such that possibly individual dentists can afford to maintain a supply. Thus the desired set of blocks can be simply selected and mounted in an articulator to quickly enable the patient's jaw movements to be simulated.

Naturally for those patient's having unusual jaw movements such that they do not fall into the standarized categories, the more precise technique of making a custom set of analogue blocks may be employed if desired. Also, it should be understood that the number of standardized categories can be increased to improve precision. For example, further breakdowns in any of the variables in the chart of FIG. 39 can be employed. Introducing additional variables or further refinements of the increments would eventually make the selection process somewhat difficult for an individual. Thus, the information could be stored in a computer and the computer programmed to receive the patient's jaw measurements and make the proper selection of analogue blocks amongst the standardized categories.

With the electronic monitoring means for measuring jaw movements, the number of classifications is almost infinite, but the number of standard sizes would have to be kept at a realistic level to maintain the practicality of the system. If the computer could not match a specific patient's jaw measurements to any of the stock selections it would indicate that this individual's movements were significantly different from all of the others. In this case this patient should be recorded with the Lee method in the above-identified patent and other related Lee patents.

c. Adjustably Mounted Preformed Guide Blocks

Figure 22:
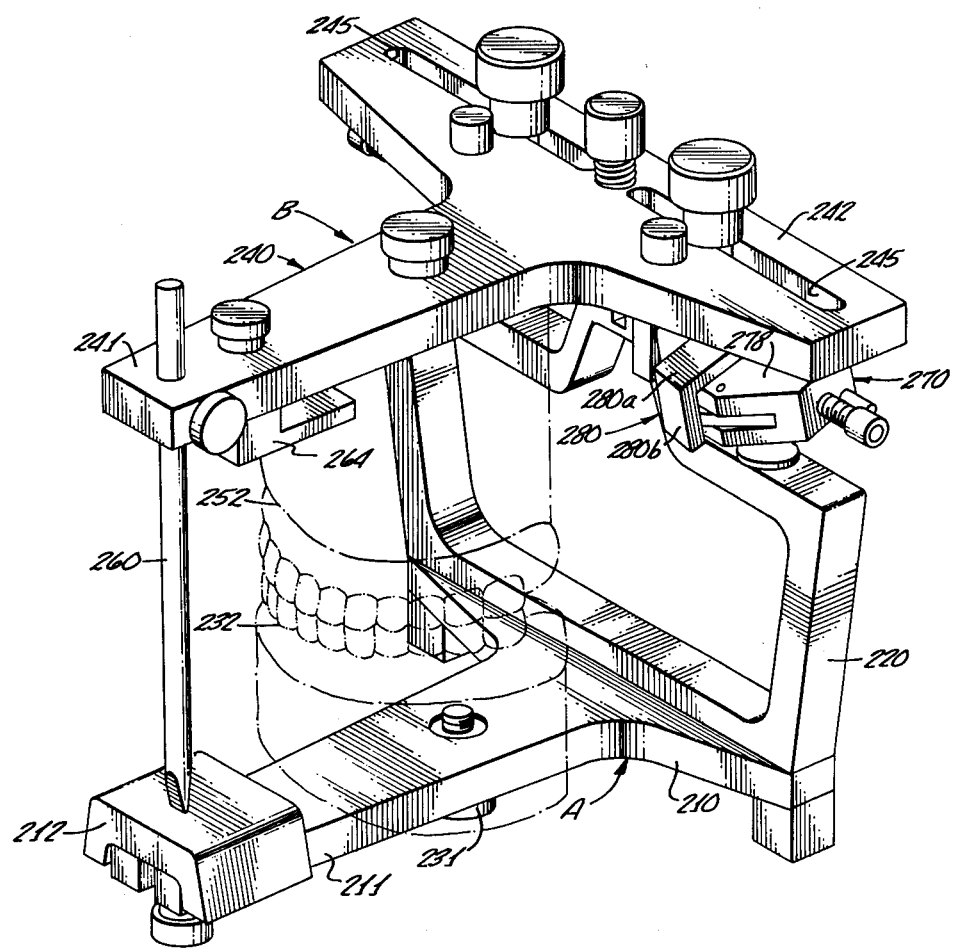
FIG. 22 is a perspective view of a jaw movement simulator.

It is contemplated that the analogue guide blocks illustrated in FIG. 28 and discussed in connection with the chart of FIG. 29 be mounted to the upper frame of a dental articulator of the type shown in FIG. 22 in a fixed manner. In one arrangement, this may be done by means of a lug formed integral with the side of the block, not shown, the lug being sized to fit within the slot 245 shown in FIG. 22. A retaining screw may be threaded into the lug to hold the block in position. Further details of such blocks and that mounting arrangement are in U.S. Pat. No. 3,694,919. In another arrangement, also discussed in that patent, the blocks are mounted in box-like housings that are in turn clamped to the upper frame of the articulator.

In an alternative simplified approach, however, the number of analogue blocks required may be reduced by mounting the blocks so that they are rotatably adjustable about the hinge axis. Such an arrangement is disclosed in connection with FIGS. 30-35. In FIG. 31, there is shown an analogue guide block 300 having a metal mounting pin 302 extending outwardly from the medial side of the block. The pin is secured in the block as the block is molded or it may be attached by other suitable means. The pin 302 terminates within the block before reaching the opening 304; however, the pin is positioned so that its axis 300a passes through the rear portion of the opening 304 coincident with the hinge axis of the articulator when the block is mounted on an articulator. The hinge axis is of course that axis which extends through the centers of the styluses in the articulator. The upper and lower frames of an articular can pivot or hinge about this axis when the upper frame is in centric position, which is centered on the hinge axis.

Figure 30:
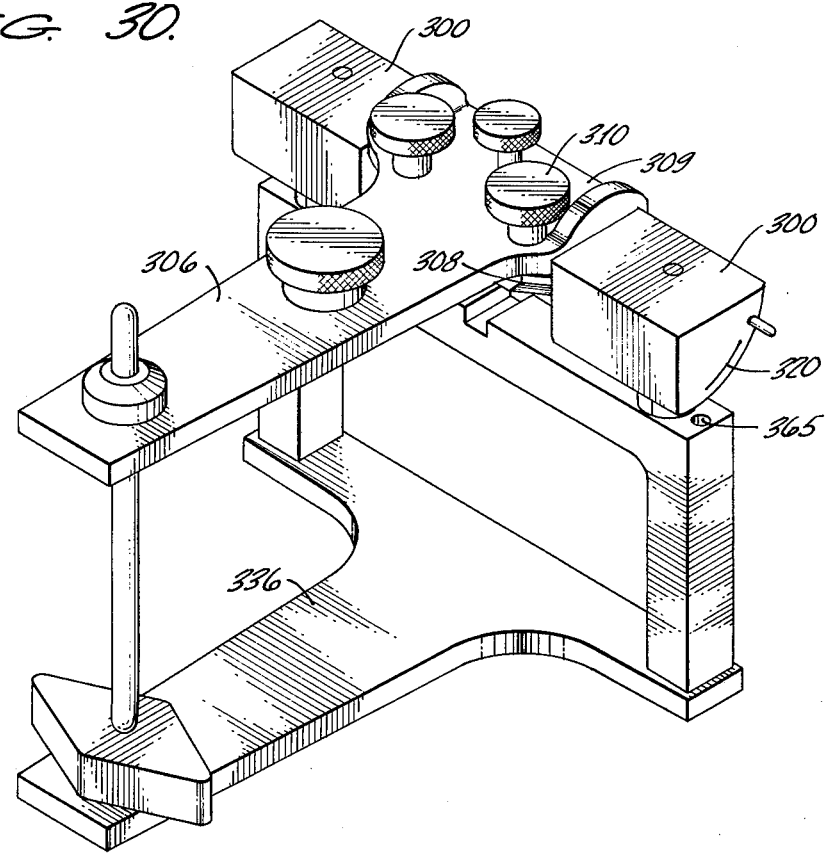
FIG. 30 is a perspective view of an articulator showing analogue guide blocks mounted so that they are rotatably adjustable.
Figure 31:
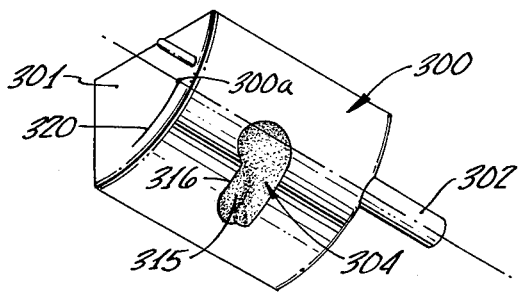
FIG. 31 is a persepective view of one of the guide blocks of FIG. 30.

FIG. 30 shows a pair of the analogue blocks 300 mounted in a simple form of articulator including an upper frame 306 having its rear portion designed to receive the mounting pin 302. More specifically, the pin 302 is clamped between a trunion plate 308, shown in FIG. 32 and the T-shaped main frame member 309. A screw 310 holds the trunion plate to the main member. The advantage of this mounting arrangment is that the guide block can be adjusted around its mounting pin to the desired angular orientation. Changing the angular orientation changes the slope or the upper wall with respect to a fixed plane of reference. This slope determines the protrusive path of the stylus 312 as it moves in the opening 315. Thus, referring to FIG. 29, a single analogue block having a specified immediate side shift is used in place of three different blocks having 30°, 45° or 60° slopes. For example, a single guide block of the type listed in FIG. 29 and having a 45° slope on its upper wall 315 can be rotated to obtain a 30° slope or a 60° slope. Since it can also be positioned at any angle between 30° and 60°, it is much more versatile than simply having the three blocks specified in Chart 29.

Rotating the guide blocks to various angular orientations simultaneously also changes the degree of horizontal slope of border path, which is the slope of the upper wall 315 adjacent the lateral 316 of the opening 304. Thus, it is not necessary to have blocks of both 45° and 60° slopes as shown in the chart of FIG. 29 since rotating the guide blocks changes the angular orientation of the guide block through that range.

Therefore, the blocks in the charge of FIG. 29 could be reduced to just having blocks of various degrees of immediately side shift and full side shift.

Furthermore, based on patient data, it has been found that there is not much variance in the angle of the medial wall after the immediate side shift. Thus, the full side shift measurement, which is the variable listed on the extreme right side of the chart in FIG. 29, is not very necessary. Consequently if that refinement is eliminated, the inventory of guide blocks specified in FIG. 29 could be replaced by simply three guide blocks having the immediate side shift dimensions specified in the chart. Further breakdowns or refinements in immediate side shift may, or course, be employed as desired.

It should also be recognized that rotating a guide block changes the nature of the side shift paths in the block as well as protrusive since the upper wall 315 is not flat. Thus, rotating the block in the manner described best duplicates both the patient's protrusive and side shift paths.

The outer lateral wall 301 of the guide block 300 is formed perpendicular to the pin 302. Inscribed or otherwise marked on the surface 301 is a curve 320 which corresponds to the protrusive path of the upper frame when moved from centric position straight forward. The curve 320 is parallel to and aligned with the protrusive path of a stylus 335 moved within the opening 304, as may be seen from FIG. 32. Such a curve 320 is useful in angularly orienting the guide block in the articulator. When a patient's jaw movements are measured and recorded as described in connection with FIGS. 1 through 20, some of the records obtained are drawings of the protrusive paths of the patient's lower jaw as measured with respect to a horizontal reference plane. More specifically, there is shown in FIG. 20 a recording plate or sheet 24 having a protrusive path P which curves downwardly and forwardly from a reference line or plane 95 passing through the point 93 which represents the hinge axis.

In FIGS. 33 and 34, there is shown a transparent sheet 322 having formed thereon a tracing or representation T1 of the protrusive path P shown on the grid sheet 24. The sheet 322 may be made of any suitable material, one being cellulose acetate having a roughened surface on the side on which the tracing is to be made. For convenience, the hinge axis on the tracing T1 is shown as the upper right hand corner 323 of the transparent sheet 322. The upper edge 325 represents the horizontal line 95 shown on the recording of FIG. 20. The sheet 322 is shown mounted on the upper frame of the articulator aligned with the hinge axis through the styluses 335 and the guide blocks. More specifically, there is provided a flat reference plate 330 which is clamped to the lower surface of the articulator frame 309 as seen in FIGS. 33 and 34. The lower surface of the articulator frame 309 defines a horizontal plane of reference which passes through the styluses 335 on the lower frame 336 and through the axes of the pins 302 when the upper frame is centrically positioned. Thus, in order to be properly aligned, the upper edge of the sheet 322 is clamped to the edge of the reference plate 330 by a clamp 332 fastened to the edge of the plate by a pair of fasteners 334. The tracing sheet 322 is adjusted both horizontally and vertically so that its edge 325 is even with the upper surface of the plate 330 which is in the horizontal plane of reference, and its upper right hand corner 323 is aligned with the axis of the pin 302 and the hinge axis through the styluses 35, as shown in FIG. 34. With the tracing sheet so positioned, it is a simple matter to angularly or rotationally adjust the position of the guide block, as shown in FIG. 34, until the curve 320 shown on the outer face of the guide block is aligned with the curve T1 on the transparent sheet 322. When the guide block is properly oriented, the fastener screw 310 is simply tightened so that the guide block is firmly fixed. The transparent sheet 322 and the mounting plate may then be removed from the articulator and the articulator used in its usual fashion.

The angular orientation of the guide book for that particular patient may conveniently be recorded in the patient's file so that the next time it is desirable to use an articulator for that particular patient, the guide block may be quickly moved to the proper angular orientation without having to use the reference plate or the tracing on the transparent sheet. As one convenient manner of recording the angular orientation of the guide block, the outer face 311 on the upper frame 309 of the articulator is marked with suitable indicia 340 that may be aligned with the upper surface 305 of a guide block 300. The only other information needed for that particular patient is the immediate side shift measurement which is explained in connection with FIGS. 6–10. Thus, the next time an articulator is to be used for a particular patient, the dentist need only look at the records to see the immediate side shift measurement, select the analogue block closest to that side shift measurement and then mounted the guide block in the articulator with the angular orientation previously determined. Also, the full side shift parameter in the chart of FIG. 29 may be used for classifying the blocks instead of immediate side shift.

The protrusive path P in FIG. 2 which extends from centric position forwardly, perpendicular to the hinge axis has been used to illustrate the mounting of the analogue blocks of FIG. 31. Other protrusive paths may also be used. Thus, the border movement path L of FIG. 20, which is part protrusive and part lateral, can be marked on the outer face of a guide block and on a tracing sheet for angularly orienting the guide block in the manner described above.

Figure 35:
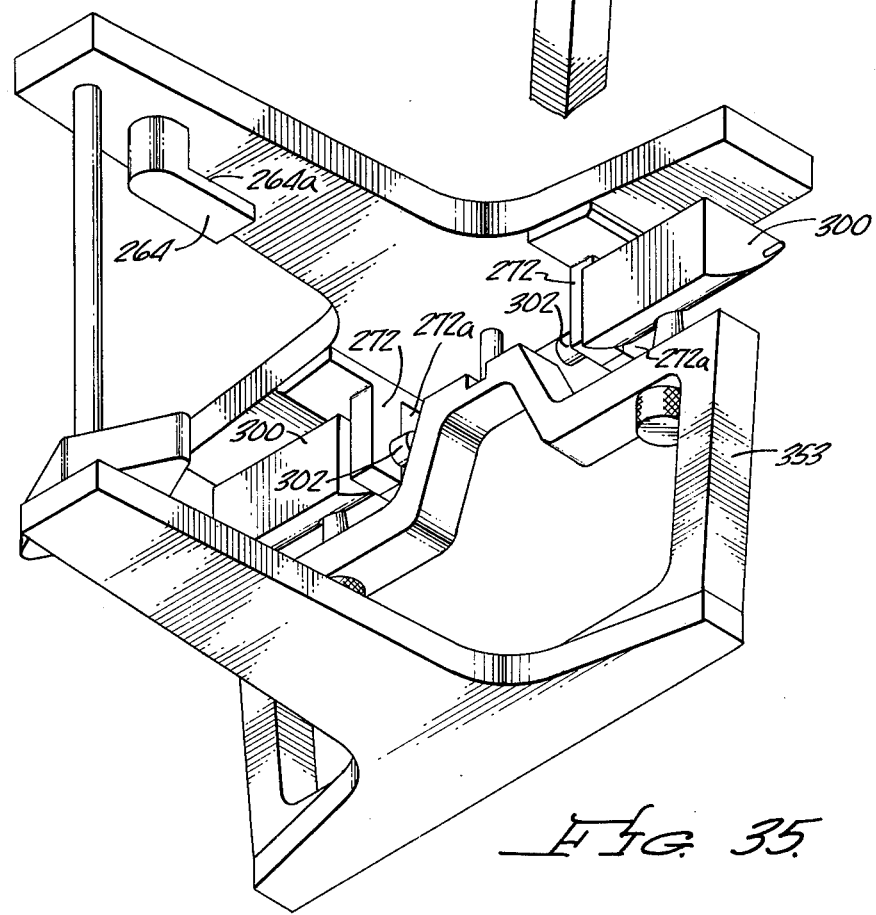
FIG. 35 is a bottom perspective view showing the analogue blocks of FIGS. 30 and 32 mounted in an articulator wherein the horizontal plane of reference is spaced below the lower surface of the upper frame of the articulator.

In FIG. 35, there is shown a pair of analogue guide blocks 300 mounted in an articulator of the type illustrated in FIGS. 22–27. In this case, the mounting pins of the guide blocks are clamped between two trunion members 272a and 273. In such an articulator, the horizontal reference plane is beneath the lower surface of the upper frame member 240. It is marked by the upper surface 264a of the flag member 264. Thus, in utilizing a tracing of the protrusive path on a transparent sheet as discussed above, it is necessary to employ a mounting arrangement which would position the tracing with its upper edge representing the horizontal reference line in the horizontal reference plane defined by the flag surface 264a and the axes of the styluses of the articulator. One way to accomplish this is, of course, to utilize a reference plate similar to plate 330 but having a mounting edge spaced the proper distance below the upper surface of the upper frame 240 so as to be aligned with the flag 264. The analogue blocks 300 may be similarly positioned in other articulators through the same techniques.

Figure 31A:
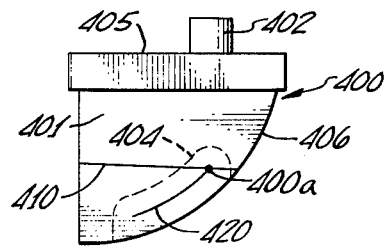
FIG. 31a is a side elevational view of a guide block to be nonrotatably mounted in an articulator.
Figure 36:
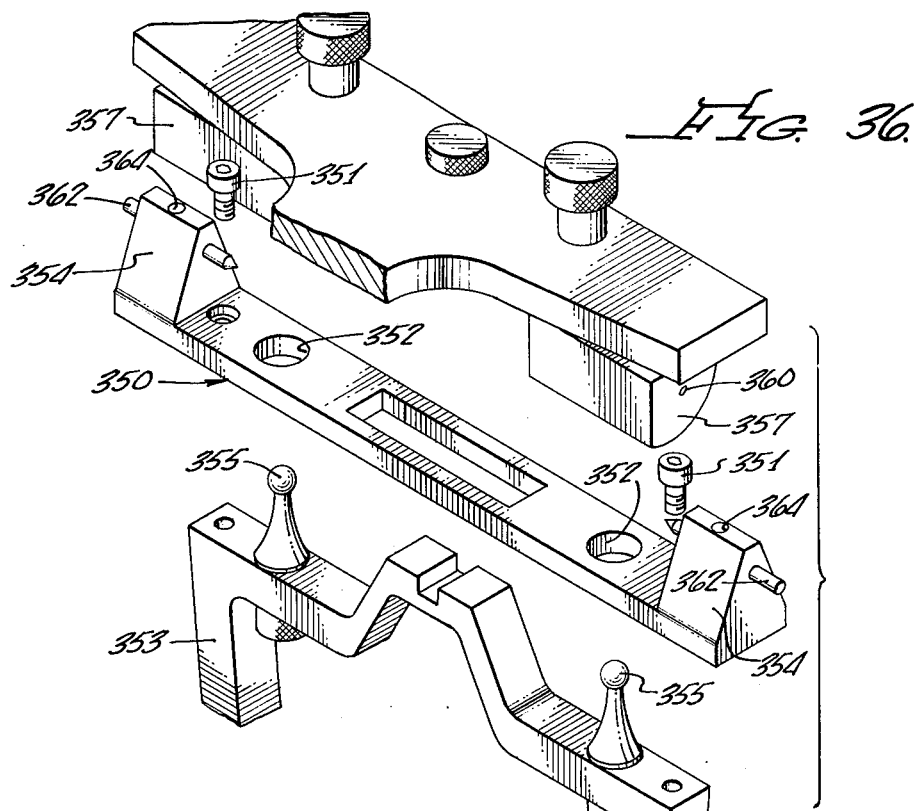
FIG. 36 is a top, exploded perspective view of a removable hinging bracket and portions of an articulator with which the bracket are used.

Referring back to FIG. 31, the feature of inscribing or otherwise marking the curve 320 on an exterior wall 301 of the block 300 is also useful for blocks that are intended to be mounted in a nonrotatable manner. Thus, in FIG. 31a there is shown a side view of an analogue guide block 400 having a mounting lug 402 extending upwardly from the upper wall 405. This lug is adapted to fit within the upper slot 245 in the upper frame of the articulator shown in FIG. 22, and thus the block cannot rotate. With such an arrangement and hinge axis 400a through the irregular opening 404 (similar to opening 304 in FIG. 31) in the lower curved wall 406 is properly positioned in a horizontal reference plane. Such a mounting arrangement s further described in U.S. Pat. Nos. 3,694,919 and 3,452,439.

Marked on the exterior, lateral wall 401 of the block 400 is a path or curve 420 which corresponds to a preselected path of the center of the articulator stylus when the stylus is moved within the opening 404. The wall 401 is perpendicular to the axis 400a and the curve 420 is parallel to the path of the center of an articulator stylus when moved within the opening 404 in a specified path, such as a protrusive path, A line 410 intersects the curve 420 and the axis 400a and is in the horizontal plane of reference for the articulator in which the block 400 will be used.

In selecting the proper set of blocks 400 from the supply of preformed blocks, a tracking sheet 322 (FIGS. 33 and 34) having a curve T1 thereon representing the same specified path of jaw movement for a particular patient as that of the block 400 is compared with the curve 420 on the exterior wall 401 of the block 400. In doing this, the upper edge 325 of the sheet 322 is aligned with the reference line 410 on the block 400 and the corner 323 of the sheet is aligned with the hinge axis 400a on the block. The alignment of the curve T1 with the curve can then be easily compared with the curve 420 on the block. With this method the different sets of standarized blocks can be quickly checked so as to select the which will most closely simulate the patient's jaw movements.

A block 400 can also be selected by checking the curve 420 after mounting the block in the articular and properly mouting the tracking sheet 322 on the articulator. With this approach, the line 410 on the block is not really needed in that the sheet 322 would be properly positioned with respect to the horizontal reference plane when mounted of the articulator. The process is repeated until the most desirable block is determined

Hinging Bracket

In using a dental articulator, is is frequently desirable to move the upper and lower frames and hinging action. One of the advantages of the articulator shown in FIG. 22 is that the pin shown extending through the lateral side wall of a guide housing in FIG. 26 may be threaded inwardly so that its inner end engages the stylus 225. With this arrangement the hinging action may be accomplished. The molded plastic analogue guide blocks discussed in connection with FIGS. 28 through37, however, there is shown an arrangement for providing this.

More specifically, there is shown an elongated flat hinge bracket 350 which is mounted on the lower frame 353 of a dental articulator by suitable fasteners 351 which thread in the frame 353. In the preferred arrangement illustrated, the bracket plate is formed with openings 352 that fit ovr the stylus 355 on the lower frame. A pair of hinge members 354 are positioned on the opposite ends of the bracket plate 350 and extend upwardly adjacent the outer or lateral faces of the guide blocks 357. Each hinge member is formed with a small hole 356 positioned to be aligned with the hinge axis 359 (FIG. 37) through the styluses 355. With the guide block properly positioned, the bit of a small hand drill 358, FIG. 37, is inserted through the hole 356 in the hinge member 354 and used to form a dimple 360 in the outer lateral surface of each guide block 357. This dimple is precisely aligned with the hinging axis 359. Such a dimple could be formed in the guide block at the time of manufacture of the block itself, but for increased accuracy, the dimple may be formed by the operator after the guide block has been positioned in the articulator. The drill is then withdrawn and hinge pins 362 are inserted in the holes in the guide member so that their inner ends fit within the dimples 360 formed in the guide blocks. The hinge pins 362 are then clamped in that position by set screws 364 and the articulator is ready for hinging action.

The bracket 350 can, of course, be used on other articulators including the one of FIG. 30 by threading the fasteners 351 into the hole 365 in the articulator base 336.

ALIGNMENT MEMBERS

In some articulators, the styluses are mounted in the lower frame a fixed distance apart, since it has been found that it is not necessary to duplicate the distance between the patient's condyles in order to obtain accurate simulation of the patient's jaw movements. Time is save by not having to make this measurement on the patient and, of course, some cost saving is made in the articulator by not having the styluses adjustably mounted. On the other hand, there are some situations, such as when mounting dental casts in an articulator, in which it is desirable or necessary to have points on the upper frame of the articulator aligned with the centric axis which may be used as reference points. For example, in utilizing a type of transfer face bow which is well known in the art, it is necessary to position a pair of face bow elements on the centric axis of the upper frame of the articulator.

For this purpose, there is shown in FIG. 38 a pair of cylindrical alignment members 370 which are mounted in the upper frame 371 of an articulator in place of a pair of guide blocks. Each cylindrical member 370 has a mounting pin 373 which is mounted in the articulator in the same manner as a guide block 300 in FIG. 32 or FIG. 35. Such members are each formed with a laterally elongated opening 374 which is received over a stylus 376. These openings 374 permit the alignment members 370 to be laterally adjustable to the desired width while still being aligned on the hinge axis through the styluses. A dimple 378 is formed in the lateral outer face of each member 370 aligned with the axis of the mounting 373 pin so that it is on the hinge axis of the articulator. In use the centric pin 372 on the upper frame 371 is positioned in the slot 382 on the lower frame 384. The members 370 are then laterally adjusted to the desired location to receive the elements of a face bow (not shown) in the dimples 378 in the outer faces of the cylindrical members. The mounting pins 373 are formed with a series of markings 373a so that the information can be recorded for subsequent use. Once the procedure utilizing a face bow is completed the alignment members 370 may be removed and replaced by the guide blocks 300 as discussed above. The members 370 can, of course, be used with the articulator of FIG. 30 as well as other articulators.

What is claimed is:

1. A method of simulating jaw movements comprising the steps of:
   measuring or registering specified parameters of a patients's lower jaw movements including side shift of the lower jaw from a predetermined location and including at least one protrusive path;
   selecting from a preformed supply of analogue guide blocks having paths formed therein of standarized sizes, classified on the basis of said lower jaw side shift, the set of blocks closest to the patient's jaw movement side shift parameters, the path in each of said blocks being adapted to receive a stylus on a dental articulator, said path having an upper wall, an inner or medial wall, and a rear wall adjacent a centic position point; and
   mounting the selected blocks in a dental articulator in a manner to receive the articulator styluses and to simulate the patient's jaw movements including rotating the blocks about the hinge axis of the articulator to the positions which will orient the guide block paths so that movement of the styluses within said block paths will best duplicate the patient's protrusive and side shift paths.

2. The method of claim 1, including the steps of:
   positioning a representation of said protrusive path adjacent the outer side of a respective one of said set of selected guide blocks with the hinge axis of the representation properly aligned with said articulator hinge axis and with a horizontal reference line on the representation aligned with a horizontal plane of reference on the articulator;
   rotating said guide block about said articulator hinge axis to align a protrusive path in the guide block with the path shown on said representation; and
   fixing the guide block in this aligned position.

3. The method of claim 2, wherein during said positioning step the representation is mounted on a reference plate on the articulator having a surface aligned with said horizontal plane of reference.

4. The method of claim 2, wherein said guide block has a path on its lateral face which corresponds to said path in the guide block and the path on the lateral face is aligned with the path on said representation.

5. The method of claim 1, wherein said protrusive path extends from said hinge axis forwardly, perpendicular to said hinge axis.

6. The method of claim 5, wherein said predetermined location is the centric relation position of said patient's jaws and said side shift is the immediate side shift of the patient's condyles.

7. The method of claim 1, wherein said protrusive path is the protrusive component of the border movement path obtained by twisting jaw movement in which one condyle moves primarily protrusively while the other condyle shifts primarily sideways.

8. The method of claim 1, including:
   recordng the measurement of said path on a thin flat sheet;

tracing the recording of the path onto a transparent sheet;

positioning said transparent sheet adjacent the outer side of a respective one of said selected set of said guide blocks with the path on the transparent sheet properly aligned with respect to said hinge axis of the articulator and with the horizontal reference line on the transparent sheet aligned with the horizontal plane of reference on the articulator;

positioning the guide block to align a path on the guide block to correspond with the path shown on said transparent sheet; and fixing the guide block in this aligned position.

9. Dental apparatus for simulating human jaw movements comprising:

a dental articulator lower frame having a pair of spaced styluses;

a dental articulator upper frame including a pair of guide blocks having openings for receiving said styluses, said guide blocks being selected from a supply of blocks wherein said openings are preformed with fixed surfaces to guide styluses of an articulator to provide simulated human jaw movement, said fixed surfaces including an upper wall, an inner or medial wall, and a rear wall, said pair of guide blocks being selected to most closely simulate the side shift of the patient for whom the articulator is being used, and including means for mounting said blocks to be rotatably adjustable in the articulator around the hinge axis extending through the center of said styluses so that the blocks may be fixed in a position to enable said patient's protrusive jaw movement to be simulated.

10. The apparatus of claim 9, including a mounting pin attached to each of said guide blocks, the pin axis being on said hinge axis when the styluses are positioned in said guide blocks in centric relation position, and means on said upper frame for supporting the mounting pin in a fixed position after it has been rotated to a desired position based on previously measured information of the patient's jaw movements.

11. The apparatus of claim 10, wherein said pin is molded in said guide block.

12. The apparatus of claim 9, including:

a reference plate mounted to the upper frame of the articulator having a surface aligned with a horizontal plane of reference;

means representing a protrusive path of said patient's jaw movement mounted on said reference plate adjacent the outer surface of one of said guide blocks with said path being properly aligned with said hinge axis, and a reference line on said means being aligned with said surface on said reference plate so that the adjacent guide block may be rotated until a path on the outer face of the guide block is aligned with the path on said representing means; and means for fixing said guide block in said aligned position.

13. An analogue guide block having a fixed pathway molded therein for use in a dental articulator to simulate the jaw movements of a human patient, said articulator having a pair of spaced styluses, each of which is to be received within a fixed pathway of one of said guide blocks, and said block having a mounting pin attached to said block and extending outwardly from the block, said pin being adapted to be received within the upper frame of said articulator and being mounted to permit adjustment of said block about an axis of the articulator.

14. The guide block of claim 13, wherein said pin is molded in place in said block.

15. The guide block of claim 13, including means formed on the outer side of said block defining a path which corresponds to a path of said articulator stylus when moved in said pathway.

16. An analogue guide block for use in a dental articulator having a pair of spaced styluses defining a hinge axis to simulate the jaw movements of a human patient, said block having a fixed pathway formed therein to receive the stylus of the articulator and having an exterior surface which is generally perpendicular to said axis when the styluses are positioned in said pathway of a pair of said blocks in centric position, and means formed on said exterior surface of said block defining a path which intersects said centric axis and corresponds to a specified path of an articulator stylus when moved in said pathway.

17. An alalogue guide block for use in a dental articulator to simulate jaw movements, said block having a pathway formed therein for receiving one of a pair of spaced styluses defining a hinge axis, said block having an exterior surface which is generally perpendicular to said axis when the styluses are positioned in centric position in the pathway of a pair of said blocks and means formed on exterior of said block defining a path which intersects said axis when the articulator is in centric position and which corresponds to said pathway in a manner such that a recording of a patient's jaw movement path may be compared with said exterior path on the block to determine whether the block can be used to closely simulate the patient's jaw movements.

18. The block of claim 17, including a reference line on the exterior surface which intersects said path and is to be aligned with a reference line on said recordng path and said exterior path.

19. The method of simulating jaw movements comprising the steps of:

recording a path of a patient's jaw movement, said path intersecting the patient's jaw hinge axis;

selecting from a preformed supply of analogue guide blocks, having standardized pathways for receiving the styluses of a dental articulator, the set of blocks which most closely simulate th patient's jaw movements when used in the articulator, said styluses defining a hinge axis, said selection being made by comparing the recorded path with a path on the exterior of one of said blocks which intersects said stylus hinge axis when the styluses are in centric position and which corresponds to said pathway within the block.

20. The method of claim 19, wherein the recorded path is in the form of a curve marked on a transparent sheet, and said comparing is made by aligning the curve on said sheet with the path on the exterior of said block including the aligning of said intersections.

21. A dental articulator comprising:

a lower frame having a pair of styluses fixed in spaced relation;

an upper frame including a pair of guide blocks having openings formed therein for receiving said styluses;

a hinging bracket mounted on said lower frame having a pair of hinge members positioned outwardly from said styluses and each having a hole formed therein aligned with the hinge axis through the centers of said styluses; and laterally adjustable pins extending through said holes to engage mating recesses in the outer faces of said guide blocks so that said upper frame may be pivoted with respect to said lower frame about said pins.

22. The articulator of claim 21, wherein said bracket is formed with holes through which said styluses extend when the bracket is mounted on said lower frame.

23. A dental articulator comprising:

a lower frame having a pair of styluses fixed in spaced relation;

an upper frame having means for mounting a pair of alignment members each having a laterally elongated opening for receiving said styluses; and dimples formed in the outer ends of said members aligned with said styluses for receiving a transfer face bow utilized in connection with mounting dental items onto the articulator, said members being laterally adjustable in said upper frame so as to accommodate face bows set to various face widths.

24. The articulator of claim 23, including mounting pins attached to said alignment members for mounting the members in said upper frame, said pins having means for indicating the lateral adjustment of said members in the upper frame.

* * * * *